US007887816B2

(12) United States Patent
Feldman et al.

(10) Patent No.: US 7,887,816 B2
(45) Date of Patent: *Feb. 15, 2011

(54) ATTENUATED MICROORGANISMS FOR THE TREATMENT OF INFECTION

(75) Inventors: Robert Graham Feldman, Berkshire (GB); Gordon Dougan, Berkshire (GB); Joseph David Santangelo, Berkshire (GB); David William Holden, Berkshire (GB); Jacqueline Elizabeth Shea, Berkshire (GB); Zoe Hindle, Berkshire (GB)

(73) Assignee: Emergent Product Development UK Limited, Berkshire (GB)

( * ) Notice: Subject to any disclaimer, the term of this patent is extended or adjusted under 35 U.S.C. 154(b) by 206 days.

This patent is subject to a terminal disclaimer.

(21) Appl. No.: 11/701,214

(22) Filed: Feb. 1, 2007

(65) Prior Publication Data

US 2008/0274139 A1 Nov. 6, 2008

Related U.S. Application Data

(63) Continuation of application No. 10/822,053, filed on Apr. 8, 2004, now Pat. No. 7,211,264, which is a continuation of application No. 09/569,601, filed on May 9, 2000, now Pat. No. 6,756,042.

(30) Foreign Application Priority Data

May 10, 1999 (GB) ................................. 9910812.8

(51) Int. Cl.
*A61K 39/112* (2006.01)
*C12N 1/12* (2006.01)

(52) U.S. Cl. ................................. 424/258.1; 435/252.1
(58) Field of Classification Search ........................ None
See application file for complete search history.

(56) References Cited

U.S. PATENT DOCUMENTS

| | | | |
|---|---|---|---|
| 4,440,859 A | 4/1984 | Rutter | |
| 4,530,901 A | 7/1985 | Weissmann | |
| 4,550,081 A | 10/1985 | Stocker | |
| 4,582,800 A | 4/1986 | Crowl | |
| 4,677,063 A | 6/1987 | Mark | |
| 4,704,362 A | 11/1987 | Itakura | |
| 4,710,463 A | 12/1987 | Murray | |
| 4,757,006 A | 7/1988 | Toole | |
| 4,766,075 A | 8/1988 | Goeddel | |
| 4,810,648 A | 3/1989 | Stalker | |
| 4,837,151 A | 6/1989 | Stocker | |
| 5,210,035 A | 5/1993 | Stocker | |
| 5,356,797 A | 10/1994 | Nielsen | |
| 5,397,697 A | 3/1995 | Lam | |
| 5,527,674 A | 6/1996 | Guerra | |
| 5,618,666 A | 4/1997 | Popoff | |
| 5,643,579 A | 7/1997 | Hung et al. | |
| 5,700,683 A | 12/1997 | Stover | |
| 5,700,928 A | 12/1997 | Hodgson | |
| 5,876,931 A | 3/1999 | Holden | |
| 6,015,669 A | 1/2000 | Holden | |
| 6,251,406 B1 | 6/2001 | Haefliger | |
| 6,342,215 B1 | 1/2002 | Holden | |
| 6,458,368 B1 | 10/2002 | Haeflinger | |
| 6,585,975 B1 | 7/2003 | Kleanthous | |
| 6,756,042 B1* | 6/2004 | Feldman et al. | ............ 424/258.1 |
| 6,846,667 B1 | 1/2005 | Crooke | |
| 6,936,425 B1 | 8/2005 | Hensel | |
| 6,951,732 B2 | 10/2005 | Clarke | |
| 6,984,490 B1 | 1/2006 | Holden | |
| 7,211,264 B2* | 5/2007 | Feldman et al. | ............ 424/258.1 |
| 7,449,178 B2 | 11/2008 | Crooke | |
| 2004/0203039 A1 | 10/2004 | Hensel | |
| 2006/0216309 A1 | 9/2006 | Holden | |
| 2008/0075739 A1 | 3/2008 | Hensel et al. | |
| 2008/0175866 A1 | 7/2008 | Holdon | |

FOREIGN PATENT DOCUMENTS

| | | |
|---|---|---|
| EP | 0889120 | 1/1999 |
| EP | 0889120 B1 | 1/1999 |
| WO | WO 9201056 | 1/1992 |
| WO | WO 9220805 | 11/1992 |
| WO | WO 9304202 | 3/1993 |

(Continued)

OTHER PUBLICATIONS

Medina, E. et al. "Pathogenicity Island 2 Mutants of *Salmonella typhimurium* Are Efficient Carriers for Heterologous Antigens and Enable Modulation of Immune Responses", *Infection and Immunity*, 1999, pp. 1093-1099, vol. 67, No. 3.

(Continued)

*Primary Examiner*—Mark Navarro
(74) *Attorney, Agent, or Firm*—Cooley LLP

(57) ABSTRACT

The present invention pertains to a *Salmonella* microorganism having an attenuating mutation which disrupts the expression of a gene located within the Spi2 pathogenicity island, and an auxotrophic mutation. The microorganism therefore has a double mutation which helps prevent reactivity of the microorganism while maintaining the effectiveness of the microorganism to elicit an immune response. The present invention also pertains to vaccine compositions and methods for treating and preventing a *Salmonella* infection in a patient.

37 Claims, No Drawings

FOREIGN PATENT DOCUMENTS

| | | |
|---|---|---|
| WO | WO 9310246 | 5/1993 |
| WO | WO 9411024 | 5/1994 |
| WO | WO 9426933 | 11/1994 |
| WO | WO 9611708 | 4/1996 |
| WO | WO 96/17951 | 6/1996 |
| WO | WO 9617951 | 6/1996 |
| WO | WO 9718225 | 5/1997 |
| WO | WO 9806428 | 2/1998 |
| WO | WO 9835562 | 8/1998 |
| WO | WO 9901473 | 1/1999 |
| WO | WO 9945120 | 9/1999 |
| WO | WO 00/14240 | 3/2000 |
| WO | WO 0014240 | 3/2000 |
| WO | WO 0132697 | 5/2001 |
| WO | WO 0185772 | 11/2001 |
| WO | WO 03044047 | 5/2003 |

OTHER PUBLICATIONS

Valentine, P.J. et al. "Identification of Three Highly Attenuated *Salmonella typhimurium* Mutants That Are More Immunogenic and Protective in Mice than a Prototypical *aroA* Mutant", *Infection and Immunity*, 1998, pp. 3378-3383, vol. 66, No. 7.

Hensel, M. et al. "Genes Encoding Putative Effector Proteins of the Type III Secretion System of *Salmonella* Pathogenicity Island 2 are Required for Bacterial Virulence and Proliferation in Macrophages", *Molecular Microbiology*, 1998, pp. 163-174, vol. 30, No. 1.

Hensel, M. et al. "Analysis of the Boundaries of *Salmonella* Pathogenicity Island 2 and the Corresponding Chromosomal Region of *Escherichia coli* K-12", *Journal of Bacteriology*, 1997, pp. 1105-1111, vol. 179, No. 4.

Hensel, M. et al. "Functional Analysis of ssaJ and ssaK/U Operon, 13 Genes Encoding Components of the Type III Secretion Apparatus of *Salmonella* Pathogenicity Island 2", *Molecular Microbiology*, 1997, pp. 155-167, vol. 24, No. 1.

Shea, J.E. et al. "Influence of the *Salmonella typhimurium* Pathogenicity Island 2 Type III Secretion System on Bacterial Growth in the Mouse", *Infection and Immunity*, 1999, pp. 213-219, vol. 67, No. 1.

Shea, J.E. et al. "Identification of a Virulence Locus Encoding a Second Type III Secretion System in *Salmonella typhimurium*", *Proc. Natl. Acad. Sci. USA*, 1996, pp. 2593-2597, vol. 93.

Chatfield, S. N. et al. "Construction of a Genetically Defined *Salmonella typhi* Ty2 aroA, aroC Mutant for the Engineering of a Candidate Oral Typhoid-Tetanus Vaccine", *Vaccine*, 1992, pp. 53-60, vol. 10, No. 1.

Levine, M.M. et al. "Attenuated *Salmonella* as Live Oral Vaccines Against Typhoid Fever and as Live Vectors", *Journal of Biotechnology*, 1996, pp. 193-196, vol. 44, No. 1-3.

Dougan, G. et al. "Live Bacterial Vaccines and Their Application as Carriers for Foreign Antigens", *Advances in Veterinary Science and Comparative Medicine*, 1989, pp. 277-300, vol. 33.

Hohmann, E.L. et al. "Evaluation of a phoPlphoQ-deleted, *aroA*-deleted Live Oral *Salmonella typhi* Vaccine Strain in Human Volunteers", *Vaccine*, 1996, pp. 19-24, vol. 14, No. 1.

Lowe, D.C. et al. "Characterization of Candidate Live Oral *Salmonella typhi* Vaccine Strains Harboring Defined Mutations in *aroA*, *aroC*, and *htrA*", *Infection and Immunity*, 1999, pp. 700-707, vol. 67, No. 2.

Schodel, F. et al. "Hepatitis B Virus Nucleocapsid/pre-S2 Fusion Proteins Expressed in Attenuated *Salmonella* for Oral Vaccination", *Journal of Immunology*, 1990, pp. 4317-4321, vol. 145, No. 12.

Plotkin, S. A. *Vaccines*, 1988, p. 571, W.B Saunders Co., Philadelphia.

Ochman, et al. "Identification of a pathogenicity island required for *Salmonella* survival in host cells," Proc. Natl. Acad. Sci. USA, 1996, pp. 7800-7804, vol. 93.

Abaev, et al. (1997) "Stable expresion of heterologous proteins in Salmonella: Problems and approaches to their designing," Vestn. Ross Akad Med Nauk 6:48-52 Abstract Only.

Agrawal and Goodchild (1987) "Oligodeoxynucleotide methylphosphonate: synthesis and enzymatic degradation." Tetrahedron Letters, 28:3536-3542.

Agrawal and Tang (1990) "Efficient synthesis of oligoribonucleotide and its phosphorothioate analogue using H-Phosphonate Approach," Tetradhedron Letters, 31:7541-7544.

Agrawal (1998) "Oligodeoxynucleoside phosphoramidates and phosphorothioates as inhibitors of human immunodeficiency virus," PNAS 85:7079-7083.

Agrawal (1990) "Site-specific excision from RNA by RNase H and mixed phosphate-backbone oligodeoxyribonucleotides." PNAS 87:1401-1405.

Agrawal et al. (1991) "Pharmacokinetics, biodistribution and stability of oligodeoxynucleotide phosphorothioates in mice," PNAS, 88:7595-7599.

Allaoui, et al. (1993) "MxiD, an outer membrane protein necessary for the secretion of Shigella flexneri Ipa invasins," Mol. Microbiol., 7:59-68.

Altmeyer, et al. (1993) "Cloning and molecular characterization of gene involved in Salmonella adherence and invasion of cultured epithelial cells," Mol. Microbiol., 7:89-98.

Andrews and Maurelli (1992) "MxiA of Shigella flexneria 2a, which facilitates export of invasion plasmid antigens encodes a homol of low-calcium-response protein LcrD, of *Yersinia pestis*," Infect. Immun. 60:3287-3295.

Bachman (1990) "Linkage map of *E. coli* K-12," Micro. Rev. 54:130-197.

Bajaj, et al. (1996) "Co-ordinate regulation of *Salmonella typhimurium* invasion genes by environmental and regulatory factor is mediated by control of expression," Mol. Microbiol. 18:715-727.

Bajaj, et al. (1995) "*hilA* is notvel *ompR/toxR* family member that activates the expression of *Salmonella typhimurium* invasion genes." Mol. Microbiol. 18:715-727.

Bannwarth (1988) "Solid-phase synthesis of oligodeoxynucleotides containing phosphoramidate internucleotide linkages and their specific chemical cleavage," Helv. Chim. Acta. 71:1517-1527.

Baudry, et al. (1988) "Nucleotide sequence of the invasion plasmid antigen B and C genes (ipaB and ipaC) of *Shigella flexneri*," Microb. Pathog. 4:345-357.

Benson and Goldman (1992) "Rapid mapping in *Salmonella typhimurium* with Mud-P22 prophages," J. Bacteriol. 175:1673-1681.

Boddikcer, et al. (2006) "Signature-tagged mutagenesis of *Klebsiella pneumoniae* to identify genes that influence biofilm formation on extracellular matrix material," Infect. Immun. 74:4590-4597.

Bogdanove, et al. (1996) "Unified nomenclature for broadly conserved hrp genes of phytopathogenic bacteria," Mol. Microbiol. 20:681-683.

Bourgogne, et al. (1998) "*Salmonella abortusivusm* strain RV6, new vaccinal vehicle for small ruminants," Vet. Microbiol. 61:199-213 Abstract Only.

Cardenas, et al. (1994) "Influence of strain viability and antigen done on the use of attenuated mutants of Salmonella as vaccine carriers," Vaccine 12:883-840.

Cardenas, et al. (1993) "Stability, immunogenicity and expression of foreign antigens in bacterial vaccine vectors," Vaccine 11:122-125 Abstract Only.

Cardenas, et al. (1992) "Oral administration using live attenuated Salmonella spp. as carriers of foreign antigens," Clin. Microbiol. Rev. 5:328-342.

Cattozzo, et al. (1997) "Expression of immunogenicity of V3 loop epitopes of HIV isolates SC and WMJ2, inserted in *Salmonella flagellin*," J. Biotechnol. 56:191-203 Abstract Only.

Chabalgoity, et al. (1996) "A *Salmonella typhimurium* htrA live vaccine expressing multiple copies of a peptide comprising amino acids 8-23 of herpes simplex virus glycoprotein D as a genetic fusion to tetanus toxin fragment C protects mice from herpes simplex virus infection," Mol. Microbiol. 19:791-801.

Chacon, et al. (1996) "Heterologous expression of the citicular glutathione peroxidase of lymphatic filariae in an attenuated vaccine strain of *Salmonella typhimurium* abrogates H-2 restriction of specific antibody response," Parasite Immunol. 18:307-316 Abstract Only.

Chang, et al. (1978) "Construction and characterization of amplifiable multicopy DNA cloning vehicles derived from the P15A cryptic miniplasmid" J. Bacteriol. 134:1141-1156.

Charles, et al. (1990) "Gene expression an the development of live enteric vaccines," Trends Biotechnol. 8:117-121 Abstract Only.

Chatfield, et al (1992) "Construction of a genetically defined *Salmonella typhi* Ty2 aro A, aroC mutain for the engineering of a candidate oral typhoid-tetanus vaccine," Vaccine 10:53-60.

Chatfield, et al. (1994) "The use of live attenuated *Salmonella* for oral vaccination," Dev. Biol. Stand. 82:35-42.

Chatfield, et al. (1993) "The development of oral vaccines based on live attenuated *Salmonella* strains," FEMS Immunol. Med. Microbiol. 7:1-7.

Chatfield, et al. (1995) "The development of oral vaccines against parasitic diseases utilizing live attenuated *Salmonella*," Paristology 110Suppl.:S17-S24.

Chatfield, et al. (1989) "Live *Salmonella* vaccines and carriers of foreign antigenic determinants," Vaccine 7:495-498.

Cirillo, et al. (1995) "Bacterial vaccine vectors and bacillus Calmette-Guerin," Clin. Infect. Dis. 30:1001-1009.

Clements (1987) "Use of attenuated mutants of *Salmonella* as carriers for delivery of heterologous antigens to the secretory immune system," Pathol. Immunopathol. Res. 6:137-146.

Clements (1990) "Vaccines against enterotoxigenic bacterial pathogens based on hybrid *Salmonella* that express heterologous antigens," Res. Microbiol. 141:981-993. Abstract Only.

Cohen, et al. (1990) "Microbial isopenicillin n. synthase genes: structure, function, diversity and evolution," Trends in Biotechnol. 8:105-111.

Collazo, et al. (1995) "Functional analysis of the *Salmonella typhimurium* invasion genes invl and invJ and identification of a target of the protein secretion apparatus encoded in the inv. locus," Mol. Microbiol. 15:25-38.

Cosstick and Vyle (1989) "Solid phase synthesis of oliogonucleotides containing 3'-thioymidase," Tetrahedron Letters, 30:4693:4696.

Covone, et al. (1998) "Levels of expression and immunogenicity of attenuated *Salmonella enterica servar typhimurium* strains expression *Escherichia coli* mutant heat-labile enterotoxin," Infect. Immun. 66:224-231.

Coynault, et al. (1992) "Growth phase and SpvR regulation of transcription in *Salmonella typhimurium* spvANC virulence genes," Microb. Pathog. 13:133-143. Abstract Only.

Curtiss, et al. (1990) "Stabilization of recombinant avirulent vaccine strains in vivo," Res. Microbiol. 141:797-805. Abstract Only.

Davidson, et al. (1995) "Lung disease in the cystic fibrosis mouse exposed to bacterial pathogens," Nat. Genet. 9:351-357.

De Lorenzo, et al. (1990) "Mino-Tn5 transposon derivatives for insertion mutagenesis promoter probing, and chromosomal insertion of cloned DNA in gram-negative eubacteria," J. Bacteriol. 172:6568-6572.

De Lorenzo and Timis (1994) "Analysis and Construction of of stable phenotypes in gram negative bacteria with Tn5 and Tn10-derived minitransposons," Methods Enzymol. 235:386-405.

Degroote, et al (1997) "Periplasmic superoxide dismutase protects Salmonella from products of phagocyte NADPH-oxidase and nitric oxide synthase," PNAS 94:13997-14001.

Deiweick, et al. (1999) "Environmental regulation of *Salmonella* pathogenicity island 2 gene expression," Mol. Microbiol. 31:1759-1773.

Diederich, et at. (2000) "In search for specific inhibitors of human 1 1beta-hydroxysteroid-dehydrogenases (11beta-HSDs): Chenodeoxycholic acid selectivity inhibits 1 1beta-HSD-1" Eur. J. Endocrinol. 142:200-207.

Deiwick and Hensel (1999) "Regulation of virulence genes by environmental signal in *Salmonella typhimurium* electrophoresis," 20:813-817. Abstract Only.

Doggett, et al. (1993) "Immune response to *Streptococcus sobrinus* surface protein antigen a expressed by recombinant *Salmonella typhimurium*," Infect. Immun. 61:1859-1866.

Donnenberg, et al. (1991) "Construction of an eae deletion mutant of enterophatic *Escherichia coli* using a positive-selection suicide vector," Infect. Immunol. 59:4310-4317.

Dougan, et al. (1989) "Live bacterial vaccines and their application as carrier for foreign antigen," Adv, in Vet. Sci. And Comp. Med. 33:277-300.

Dougan, et al. (1987) "Live oral *Salmonella* vaccines: potential use of attenuated strains as carriers of heterologous antigens to the immune system," Parasite Immunol. 9:151-160.

Eichelberg, et al. (1994) "Molecular and functional characterization of the *Salmonella typhimurium* invasion genes invB and invC: homology of invC to the FOF1 ATPase family of proteins," J. Bacteriol. 176:4501-4510.

Elliot, et al. (1998) "The complete sequence of the locus of enterocyte affeacement (LEE) from enteropathogenic *Escherichia coli* E2348/49," Mol. Microbiol. 28:1-4.

Everst, et al. (1995) "Expression of LacZ from the hrtA, nirB and groE promoters in a Salmonella vaccine strain: influence of growth in mammalian cells," FEMS Microbiol. Letters 126:97-101.

Fayole, et al. (1994) Genetic control of antibody responses induced against an antigen delivered by recombinant attenuated *Salmonella typhimurium*,: Infect. Immun. 62:4310-4319.

Fields, et al. (1986) "Mutants of *Salmonella typhimurium* that cannot survive within the macrophage are invirulent," PNAS 83:5189-5193.

Fierer, et al. (1993) "Expression of the *Salmonella* virulence plasmid gene spvB in cultured macrophages and nonphagocytic cells," Infect. Immun. 61:5231-5236.

Finlay, et al. (1991) "Cytoskeletal rearrangements accompanying *Salmonella* entry into epithelial cells," 99:283-296.

Finlay (1994) "Molecular and cellular mechanisms of *Salmonella* pathogenesism" Curr. Top. Microbiol. Immunol. 192:163-185.

Foulongne, et al. (2000) "Identification of *Brucella suis* genes affecting intracellular survival in an in vitro human macrophage infection model by signature-tagged transposon mutagenesis," Infect. Immun. 68:1297-1303.

Forsberg, et al. (1994) "Use of transcriptional fusions to monitor gene expression: a cautionary tale," J. Bacteriol. 176:2128-2132.

Fouts, et al. (1995) "Construction and immunogenicity of *Salmonella typhimurium* vaccine vectors that express HIV-1 gp120," Vaccine 13:1697-1705. Abstract Only.

Fouts, et al. (1995) "Construction and characterization of *Salmonella-typhi* based human immunodeficiency virus type 1 vector vaccine," Vaccine 13:561-569. Abstract Only.

Francis et al. (1992) Morphological and cytoskeletal changes in epithelial cells occur immediately upon interaction with *Salmonella typhumurium* grown under low-oxygen conditions, Mol. Microbiol. 6:3077-3087.

Gentschev, et al. (1998) "Delivery of the p67 sporozite antigen Theileria parva by using recombinant Salmonella dublin: secretion of the product enhances specific antibody responses in cattle," Infect. Immun. 66:2060-2064.

Ginnochio, et al. (1992) "Identification and molecular characterization of a *Salmonella typhimurium* gene involved in triggering the internalization of *Salmonella* into cultured epithelial cells," PNAS 89:1575-5980.

Ginnocchio, et al. (1994) "Contact with epithelial cells induces the formation of surface appendages on *Salmonella typhimurium*," Cell 76:717-724.

Guillobel, et al. (1998) "Immunization against the colonization factor antigen I of enterotoxogenic *Escherichia coli* by administration of a bivalent *Salmonella typhimurium* aroA strain," Braz. J. Med. Biol. Res. 31:545-554. Abstract Only.

Gunn and Miller (1996) "PhoP-PhoQ activates transcription of pmrAB, encoding a two-component regulatory system involved in *Salmonella typhimurium* antimicrobial peptide resistance," J. Bacteriol. 178:6857-6864.

Guy, et al. (2000) "Aggregation of host endosomes by *Salmonella* requires SPI2 translocation of SseGF and involves SpvR and the fms-aroE intergenic region," Mol. Microbiol. 37:1417-1435. Abstract Only.

Haddad, et al. (1995) "Surface display compared to periplasmic expression of a malarial antigen in *Salmonella typhimurium* and its implications for immunogencity," FEMS Immunol. Med. Microbiol. 12:175-186. Abstract Only.

Hahn, et al. (1998) A *Salmonella typhimurium* strain genetically engineered to secrete a bioactive human interleukin (hIL)-6 via the

*Escherichia coli* hemolysin secretion apparatus, FEMS Immunol. Med. Microbiol. 20:111-119. Abstract Only.

Hakansson, et al. (1996) "The YoB protein of *Yersinia pseudotuberculosis* is essential for the translocation of Yop effector proteins accrsoos the target cell plasma membrane and displays a contact-dependent membrane disrupting activity," EMBO J. 15:5812-5823.

Harokopakis et al. (1997) "Mucosal immunogenicity of a recombinant *Salmonella typhimurium*-cloned heterologous antigen in the absence or presence of co-expressed cholera toxin A2 and B subunits," Infect. Immun. 65:1445-1454.

Hauser, et al. (1998) "Defects in type III secretion correlate with internalization of *Pseudomonas aeruginosa* by epithelial cells," Infect. Immun. 66:1413-1420.

Havaarstein, et al. (1995) "An unmodified heptadecapeptide phermone induces competence for genetic transformation in *Streptococcus pneumoniae*," PNAS 92:11140-11144.

He, et al. (2000) "Function of human brain short chain L-3 hydroxyl coenzyme A dehydrogenase in androgen metabolism," Biochemica Et. Biophysica Acta:1484:267-277.

Heithoff, et al. (1999) "An essential role for DNA adenine methylation in bacterial virulence," Science 284:967-970.

Hensel and Holden (1996) "Molecular genetic approaches for the study of viruclence in both pathogenic bacteria and fungi," Microbiol. 142:1049-1058.

Herrero, et al. (1990) "Transposon vectors containing non-antibiotic resistance selection markers for cloning and stable chromosomal insertion of foreign genes in gram negative bacteria," J. Bacteriol. 172:6557-6567.

Hess, et al. (1997) "Protection against murine listerioisis by an attenuated recombinant *Salmonella typhimurium* vaccine strain that secretes the naturally somatic antigen superoxide dismutase," Infect. Immun. 65:1286-1292.

Hess, et al. (1995) "Listeria monocytogenes p60 supports host cell invasion by and in vivo survival of attenuated *Salmonella typhimurium*," Infect. Immun. 63:2047-2053.

Hess, et al. (1996) "Superior efficacy of secreted over somatic antigen display in recombinant *Salmonella* vaccine induced protection against listeriosis," PNAS 93:1458-1463.

Hess, et al. (1997) "Modulation of antigen display by attenuated *Salmonella typhimurium* strains and its impact on protective immunity against listeriosis," Behring Inst. Mitt. 160-171.

Hirakata, et al. (1992) "Efficacy of erythromycin lactobionate for treating *Pseudomonas aeuginosa* bacteremia in mice," Antimicrob. Agents Chemother. 36:1198-1203.

Hoffman and Stoffel (1993) "TMbase—a database of membrane spanning protein segments," Biol. Chem. Hoppe-Seyler 347:166.

Hohmann, et al. (1995) "Macrophage-inducible expression of a model antigen in *Salmonella typhimurium* enhances immunogenicity," PNAS 92:2904-2908.

Hohmann, et al. (1996) "Evaluation of phoP/phoQ-deleted aroA-deleted live oral *Salmonella typhi* vaccine strain in human volunteers," Vaccine 14:19-24.

Holden, et al. (1989) "Mutation in heat-regulated hsp70 gene of Ustilago maydis," EMBO J. 8:1927-1934.

Holtel, et al. (1992) "Upstream binding sequences of the XyIR activator protein and integration host factor in the xylS gene promoter region of the *Pseudomonas TOL plasmind*," Nucl. Acid Res. 20:1755-1762.

Hone, et al. (1988) "A chromosomal integration system for stabilzation of heterologous genes in *Salmonella* based vaccine strains," Microb. Pathog. 5:407-418. Abstract Only.

Hormaeche, et al. (1996) "Protection against oral challenge three months after i.v. immunization of BALB/c mice with live Aro *Salmonella typhimurium* and *Salmonella enteritidis* vaccines is serotype (species)-dependent and only partially determined by the main LPS O antigen," Vaccine 14:251-259. Abstract Only.

Hormaeche, et al. (1991) "Live attenuated *Salmonella* vaccines and their potential as oral combined vaccines carrying heterologous antigens," J. Immunol. 142:113-120. Abstract Only.

Hueck (1998) "Type III protein secretion systems in bacterial pathogens of animals and plants," Microbiol. Mol. Biol. Rev. 62:379-433.

Hueck, et al. (1995) "*Salmonella typhimurium* secreted invasion determinants are homologous to Shigella Ipa proteins," Mol. Microbiol. 18:479-490.

Jager, et al. (1988) "Oligonucleotide N-alkylphosphoramidates: synthesis and binding to polynucleotides," Biochemistry 20:7237-7246.

Janssen, et al. (1995) "Induction of the phoE promoter upon invasion of *Salmonella typhimurium* into eukaryotic cells," Microb. Pathog. 19:193-201. Abstract Only.

Jornvall, et al. (1995) "Short chain dehydrogenases/reductases (SDR)" Biochemistry 34:6003-6013.

Jornvall, et al. (1999) "SDR and MDR: Completed genome sequences show these protein familes to be large, of old origin and complex nature," FEBS Letters 445:261-264.

Kaniga, et al. (1995) "Homologs of the Shigella Ipa and IpC invasins are required for *Salmonella typhimurium* entry into cultured epithelial cells," J. Bacteriol. 177:3965-3971.

Kaniga, et al. (1994) "The *Salmonella typhimurium* invasion genes invF and invG encode homologs of the AraC and PuID family of proteins," Mol. Microbiol. 13L555-568.

Karem, et al. (1996) "Cytokine expression in the gut associated lymphoid tissue after oral administration of attenuated *Salmonella* vaccine strains," Vaccine 14:1495-1502. Abstract Only.

Kirsch and Di Domenico (1993) "The discovery of natural products with a therapeutic potential," V.P. Gallo, Ed. Chapter 6, pp. 1770221, Buttersworth, V.K.

Krul, et al. (1996) "Induction of an antibody response in mice against human papilloma virus (HPV) type 16 after immunization with HPV recombinant *Salmonella* strains," Cancer lmmunol. 43:44-48.

Kuwajila, et al. (1989) "Export of N-terminal fragment of *Escherichia coli* flagellin by a flagellum-specific pathway," PNAS, 86:4953-4957.

Laemmli (1970) "Cleavage of structural proteins during the assembly of the head of bacteriophage T4," Nature 227:680-685.

Leary, et al. (1997) "Expression of an Fl/V fusion protein in attenuated *Salmonella typhimurium* and protection of mice against plague," Microb. Pathog. 23:167-179. Abstract Only.

Lee, et al. (1992) "Identification of a *Salmonella typhimurium* invasion locus by selection for hyperinvasive mutants," PNAS 89:1847-1851.

Leiter, et al. (1990) "Inhibition of influenza virus replication by phosphorothioate oligodeoxynucleotides," PNAS 87:3430-3434.

Lenz, et al. (2000) "Chemical ligands, genomics and drug delivery," Drug Discovery Today 5:145-156.

Levine, et al. (1996) "Attenuated *Salmonella* as live oral vaccines against typhoid fecer and as live vectors." J. Biotechnol. 44(1-3):193-196.

Liljevist, et al. (1996) "A novel expression system for *Salmonella typhimurium*, allowing hight production levels, product secretion and efficient recovery," Biochem. Biophys. Res. Com. 218:356-359. Abstract Only.

Lingberg (1995) "The history of live bacterial vaccines," Dev. Biol. Stand. 84:211-219. Abstract Only.

Li, et al. (1995) "Relationship between evolutionary rate and cellular location among the Inv/Spa invasion proteins of *Salmonella enterica*," PNAS 92:7252-7256.

Lo-Man, et al. (1996) "Control by H-2 genes of the Th1 response induced against foreign antigen expressed by attenuated *Salmonella typhimurium*," Infect. Immun. 64:4424-4432.

Lowe, et al. (1999) "Characterization of candidate live oral *Salmonella typhi* vaccine strains harboring defined mutations in aroA, aroC and htrA" Infect. Imm. 67:700-707.

Macnab (1996) "Flagella and motility in *Escherichia coli* and *Salmonella*: cellular and molecular biology," F.C. Neidardt, et al. (eds.) Washington, D.C.:ASM Press: 123-145.

Maskell, et al . (1987) "*Salmonella typhimurium* aroA mutants as carriers of *Escherichia coli* heat labile enerotoxin B subunit to the murine secretory and systemic immune systems," Microb. Pathog. 2:2211-221. Abstract Only.

Maurer, et al. (1984) "Functional interchangeability of DNA replication genes in *Salmonella typhimurium* and *Escherichia coli* demonstrated by a general complementation procedure," Genetics 108:1-23.

McSorley, et al. (1997) "Vaccine efficacy of *Salmonella* strains expressing glycoprotein 63 with different promoters," Infect. Immun. 65:171-178.

Michiels, et al. (1991) "Analysis of virC, an operon involved in the secretion of Ypo proteins by Yersinea enterocolitica," J. Bacteriol. 173:4994-5009.

Milich, et al. (1995) "The hepatitis nucleocapsid as a vaccine carrier moiety," Ann. NY Acad. Sci. 754:187-201. Abstract Only.

Miller and Mekalanos (1998) "A novel suicide vector and its use in construction of inversion mutations: osmoregulation of outer membrane proteins and virulence determinants in Vibrio cholerae requires ToxR," J Bacteriol. 170:2575-2593.

Miller et al. (1993) "The PhoP virulence regulon and live oral Salmonella vaccines," Vaccine 11:122-125.

Minamino, et al (1999) "Components of the *Salmonella flagellar* export apparatus and classification of export substrates," J. Bacteriol. 181:1388-1394.

Miras, et al. (1995) "Nucleotide sequence of iagA and iagB genes involved in invasion of HeLa cells by *Salmonella enterica* subsp. Enterica Ser. Typhi" Res. Micorbiol. 146:17-20.

Monack, et al. (1996) "*Salmonella typhimurium* invasion induces apoptosis in infected macrophages," PNAS 93:9833-9838.

Newton, et al. (1995) "Studies of the anaerobically induced promoter pnirB and the improved expression of bacterial antigens" 146:193-202.

Nielson, et al. (1998) "Synthesis and characterization of dinucleoside phosphorodithoates," Tetrahedron Letters, 29:2911-2914.

Ocallaghan and Charbit (1990) "High efficiency transformation of *Salmonella typhimurium* and *Salmonella typhi* by electroporation," Mol. Gen. Genet. 223:156-158.

Obeysekere et at (1998) "Serines at the active site of 11 beta-hydroxysteroid dehydrogenase type 1 determine the rate of catalysis" Biochem. Biophys. Res. Commun. 250:469-473.

Ohara, et al. (1989) "Direct genomic sequencing of bacterial DNA: the pyruvate kinase I gene of *Escherichia coli*," PNAS 86:6883-6887.

Okahashi, et al. (1996) "Oral immunization of interleukin-4 (IL-4) knockout mice with a recombinant *Salmonell* strain or cholera toxin reveals CD4+ Th2 cells producing IL-6 and IL-10 are associated with mucosal immunoglobulin A responses," Infect. Immun. 64:1516-1525.

Opperman, et al. (1997) "Structure function relationships of SDR hydroxysteroid dehydrogenases," Advances in Exp. Med. and Biol. 414:403-415.

Orr, et al. (1999) "Expression and immunogenicity of a mutant diptheria toxin molecule, CRM197, and its fragments in *Salmonella typhi* vaccine strain CVD 908-htrA" Infect. Immun. 67:4290-4294.

Pallen, et al. (1997) "Coiled-coil domains in proteins secreted by type III secreion systems," Mol. Microbiol. 25:423-425.

Pearce, et al (1993) "Genetic identification of exported proteins in *Streptococcus pneumoniae*," Mol. Microbiol. 9:1037-1050.

Perlman and Freedman (1971) "Experimental endocarditis. II Staphlococcol infection of the aortic valve following placement of polyethylne catheter in the left side of the heart." Yale J. Biol. Med. 44:203-213.

Plano, et al. (1991) "LcrD, a membrane-bound reegulator of the Yersinia pestis low-calcium response," J. Bacteriol. 173:7293-7303.

Pozza, et al.. (1998) "Construction and characterization of *Salmonella typhimurium* aroA simultaneously expressing the five pertussis toxin subunits," Vaccine 16:522-529. Abstract Only.

Ralph, et al. (1975) "Reticulum cell sarcoma: and effector cell in antibody-dependent cell-mediated immunity," J. Immunol. 114:898-905.

Reed and Muench (1938) "A simple method of estimating fifty per cent end points," Am J. Hyg. 27:493-497.

Rhen, et al. (1993) "Transcriptional regulation of *Salmonella enterica* virulence plasmid genes in cultured macrophages," Mol. Microbiol. 10:45-56. Abstract Only.

Ronson, et al. (1987) "Conserved domains in bacterial regulatory proteins that respond to environmental stimuli," Cell 49:579-581.

Roy and Coleman (1994) "Mutations in firA, encoding the seond acyltransferase in lippolysaccharide biosynthesis, affect mulitple steps in lipopolysaccharide biosynthesis," 176:1639-1646.

Saiki et al. (1988) "Primer directed enzymatic ampliifcation of DNA with a thermostable DNA polymerase," Science 4839:487-491.

Salmond and Reeves (1993) "Membrane traffic wardens and protein secretion in gram negative bacteria," Trends in Biochem. Sci. 18:7-12.

Sanderson, et al. (1995) "Genetic map of *Salmonella typhimurium*,edition VIII," Microbiol. Rev. 59:241-303.

Sanger, et al. (1977) "DNA seqeunce with chain terminating inhibitors," PNAS 74:5463-5467.

Sarin, et al. (1988) "Inhibition of acquired immunodeficiency syndrome virus by oligodeoxynucleoside methylphosphonates," PNAS 85:7448-7451.

Sasakawa, et al. (1993) "Eigh genes in region 5 that form an operon are essential for invasion of epithelial cells by *Shigella flexneria* 2a," J. Bacteriol. 175:2334-2346.

Schmitt et al. (1996) "The attenuated phenotype of a *Salmonella typhimurium* flgM mutant is related to expression of FliC flagellin," J. Bacteriol. 178:2911-2915.

Schodel, et al. (1990) "Hepatitis B Virus Nucleocapsid/pre-S2 fusion proteins expressed in attenuated Salmonella for oral vaccination" J. Immunol. 145:4317-4321.

Schodel (1990) "Oral vaccination using recombinant bacteria," Semin. Immunol. 12:341-349.

Shaw et al. (1991) "Modified deoxyoligonucleotides stable to exonuclease degradation in serum," Nucelic Acids Res. 19:747-750.

Sigwart, et al. (1989) "Effect of purA mutation on efficacy of Salmonella live-vaccine vectors," Infect. Immun. 57:1858-1861.

Skorupski and Taylor (1996) "Positive selection vectors for allelic exhange," Gene 169:47-52.

Strugnell et al (1990) "Stable expression of foreign antigens from the chromosome of *Salmonella typhimurium* vaccine strains," Gene 88:57-63. Abstract Only.

Strugnell et al. (1992) "Characterization of a *Salmonella typhimurium* aro vaccine strain expressing the p69 antigen of *Bordella pertussis*," Infect. Immun. 60:3994-4002.

Su et al. (1992) "Extracellular export of Shiga toxin B-subunit haemolysin A (C-terminus) fusion proteins expressed in *Salmonella typhimurium* aro-A mutant and stimulation of B-subunit specific antibody responses," Microb. Pathog. 13:465-476. Abstract Only.

Sullivan et al (1993) "Evaluation of the efficacy of ciprofloxacin against *Streptococcus pneumoniae* by using a mouse protection model," Antimicrob. Agents Chemother. 37:234-239.

Tacket at al. (1990) "Safety and immunogenicity, and efficacy against cholera challenge in humans of a typhoid-cholera hybrid vaccine derived from *Salmonella typhi2la*" Infect. Immun. 58:1620-1627.

Tacket et al. (1997) "Safely and immunogenicity in humans of an attenuated *Salmonella typhi* vaccine vector strain expressing plasmid encoded hepatitis B antigens stabilized by the Asd-balanced lethal vector system," Infect. Immun. 65:3381-3385.

Takeuchi (1967) "Electron microscope studies of experimental Salmonella infection. I. Penetration into the intestinal epithelium by *Salmonella typhimurium*," Am. J. Pathol. 50:109-136.

Tang et al. (1993) "Self-stabilized antisense oligodeoxynucleotide phosphorothioates: properties and anti-HIV activity," Nucleic Acids Res. 21:2729-2735.

Tijhaar et al. (1997) "Induction of feline immunodeficiency virus specific antibodies in cats with an attenuated Salmonella strain expressing the Gag protein," Vaccine 15:587-596.

Tijhaar et al. (1997) "*Salmonella typhimurium* aroA recombinants and immune-stimulating complexes as vaccine candidates for feline immunodeficiency virus," J. Gen. Virol. 46:129-138.

Uznanski et al. (1987) "Deoxyribonucleoside 3'-phosphordiamidites as substrates for solid supported synthesis of oligodeoxyribonucleotides," Tetrahedron Letters 28:3401-3404.

Valentine et al. (1996) "Induction of SIV capsid specific CTL and mucosal sIgA in mice immunized with recombinant *S. typhimurium* aroA mutant," Vaccine 14:138-146.

Van Gijsegem et al (1993) "Conservation of secretion pathways for pathogenicity determinants of plant and animal bacteria," Trends Microbiol. 1:175-180.

Veber et al. (1993) "Correlation between macrolide lung pharmacokinetics and therapeutic efficacy in a mouse model of pneumococcal pneumonia," J. Antimicrob. Chemother. 32:473-483.

Venkatesan et al. (1992) "Surface presentation of *Shigella flexneri* invasion plasmid antigens requires the products of the spa locus," J. Bacteriol. 174:1990-2001.

Verma et al. (1995) "Induction of a cellular immune response to a defined T cell epitope as an insert in the flagellin of a live vaccine strain of Salmonella," Vaccine 13:235-234. Abstract Only.

Villafane et al. (1987) "Replication control genes of plasmid pE194," J. Bacteriol. 169:4822-4829.

Viret et al. (1993) "Molecular cloning and characterization of the genetic determinants that express the complete Shigella serotype D (*shigella sonnei*) lipopolysaccharide in heterologous live attenuated vaccine strains." Mol. Microbiol. 7:239-252. Abstract Only.

Wang et al, (2006) "Application of signature tagged mutagenesis to the study of Erwina amylovora" FEMS Microbiol. Lett. 265:164-171.

Wattiau et al. (1994) "Individual chaperones required for Yop secretion by Wattiau et al. (1994) "Individual chaperones required for Yop secretion by *Yersinia* PNAS 91:10493-10497.

Whitman et al (1993) "Antibiotic treatment of experimental endocarditis due to vancomycin- and ampicillin-resistant *Enterococcus faecium*," Antimicrob. Agents Chemother. 37:2069-2073.

Whittle et al. (1997) "Immune response to a Murray Valley encephalitis virus epitope expressed in the flagellin of an attenuated strain of Salmonella," J. Med. Microbiol. 46:129-138.

Whittle and Verma (1997) "The immune response to a B-cell epitope delivered by Salmonella is enhanced by prior immunological experience," Vaccine 15:1737-1740. Abstract Only.

Wirth et al. (1986) "Highly efficient protoplast transformation system for *Streptococcus faecalis* and a new *Escherichia coli-S. Faecalis* shuttle vector," J. Bacteriol. 165:831-836.

Woods et al. (1982) "Contribution of toxin A and elastase to virulence of *Pseudomonas aeruginosa* in chronic lung infections of rats," Infect. Immun. 36:1223-1228.

Yan et al. (1996) "Mixed population approach for vaccination with live recombinant *Salmonella* strains." J. Biotechnol. 44:197-201. Abstract Only.

Yancey (1993) "Recent advances in bovine vaccine technology," J. Dairy Sci. 76:2418-2436.

Yang et al., (1990) "Oral *Salmonella typhimurium* (AroA-) vaccine expressing a major leishmanial surface ptorin (gp63) preferentially induces T helper 1 cells and protective immunity agaist leishmaniasis," J. Immunol. 145:2281-2285. Abstract Only.

Yanisch-Perron et al. (1985) "Improved M13 phage cloning vectors and host strains: nucleotide sequences of the M13mp18 and pUC19 vectors." Gene 33:103-119.

Youderain et al. (1988) "Packaging specific segments of the Salmonella chromosome locked-in Mud-P22 prophages," Genetics, 118:581-592.

Young et al (1999) "A new pathway for the secretion of virulence factors by bacteria: the flagellar export apparatus functions as a protein secretion system." PNAS 96:6456-6461.

Zhu et al. (1993) "Systemic gene expression intravenous DNA delivery into adult mice." Science 261:209-211.

Acharya et al. (1987) "Prevention of typhoid fever in nepal with the vi capsular polyscharaide of *Salmonella typhi*," NEJM, 317:1101-1104.

Ahmer et al. (1999) "*Salmonella* SirA is a global regulator of genes mediating enteropathogenesis," Mol. Microbiol. 31(3):971-982.

Altare et al. (1998) "Inherited interleukin 12 deficiency in a child with Bacille Calmette-Guerin and *Salmonella enteritidis* disseminated infection," J. Clin. Invest. 102:2035-2040.

Angelakopoulos and Hohmann (2000) "Pilot study of phoP/phoQ-deleted *Salmonella enterica* serovar Typhimurium expressing *Helicobacter pylori* urease in adult volunteers," Infect. Immun., 68:2134-2141.

Aranda et al. (1992) "*Salmonella typhimurium* activates virulence gene transcription within acidified macrophage phagosomes," PNAS, 89:10079-10083.

Arricau et al. (1998) "The RcsB-RcsC regulatory system of *Salmonella typhi* differentially modulates the expression of invasion proteins, flagellin and Vi antigen in response to osmolarity," Mol. Microbiol. 29:835-850.

Ascon, et al. (1998) "Oral immunization with a *Salmonella typhimurium* vaccine vector expressing recombinant enterotoxigenic *Eschericia coli* K99 fimbrae elicits elevated antibody titers for protective immunity," Infect. Immun. 66:5470-5476.

Attridge (1991) "Oral immunization with *Salmonella typhi* Ty21a-based clones expressing *Vibrio cholerae* O-antigen: serum bactericidal antibody responses in man in relation to pre-immunization antibody levels," Vaccine, 9:877-882.

Bao and Clements (1991) "Prior immunologic experience potentiates the subsequent antibody response when *Salmonella* strains are used as vaccine carriers," Infect. Immun. 59:3841-3845.

Barry et al. (1996) "Expression and Immunogenicity of Pertussis Toxin S1 subunit-tetanus toxin fragment C fusion in *Salmonella typhi* vaccine strain CVD 908," Infect. Immun. 64:7472-4781.

Basso et al. (2002) "Characterization of a novel intracellularly activated gene from *Salmonella enterica* serovar typhi," Infect. Immun. 70:5404-5411.

Benjamin et al. (1991) "A hemA mutation renders *Salmonella typhimurium* avirulent in mice, yet capable of eliciting protection against intravenous infection with *S. typhimurium*," Microb. Pathog. 11:289-295.

Beuzon et al. (1999) "pH-dependant secretion of SseB, a product of the SPI-2 type III secretion system of *Salmonella typhimurium*," Mol. Microbiol. 33:806-816.

Beuzon et al. (2000) "*Salmonella* maintains the integrity of its intracellular vaciole through the action of SifA," EMBO J., 19:3235-3249.

Black, et al. (1983) "Immunogenicity of Ty21a Attenuated *Salmonella typhi* given with sodium bicarbonate or in enteric-coated capsules," Develop. Biol. Stand., 53:9-14.

Bost and Clements (1995) "In vivo induction of interleukin-12 mRNA epxression after oral immunization with *Salmonella dublin* or the B subunit of *Escherichia coli* heat-labile enterotoxin," Infect. Immun. 63:1076-1083.

Brennan et al. (1994) "Differences in the immune responses of mice and sheeo ti an aromatic-dependent mutant of *Salmonella typhimurium*," J. Med. Microbiol. 41:20-28.

Brown and Hormaeche (1989) "The antibody response to salmonellae in mice and humans studied y immunoblots and ELISA," Microb. Pathog. 6:445-454.

Brown et al. (1987) "An attenuated aroA *Salmonella typhimurium* vaccine elicits humoral and cellular immunity to cloned β-galactosidase in mice," J. Infect. Dis. 155:86-92.

Browne et al. (2002) "Genetic requirements for *Salmonella*-induced cytopathology in human monocyte-derived macrophages," Infect. Immun. 70:7126-7135.

Buchmeier and Libby (1997) "Dynamics of growth and death within a *Salmonella typhimurium* population during infection of macrophages," Can. J. Microbiol. 43:29-34.

Bumann et al. (2000) "Recombinant live *Salmonella* spp. for human vaccination against heterologous pathogens," FEMS Immunol. Med. Microbiol. 27:357-364.

Bumann et al. (2002) "Safety and immunogenicity of live recombinant *Salmonella enterica* serovar typhi Ty21a expressing urease A and B from *Helicobacter pylori* in human volunteers," Vaccine, 20:845-852.

Butler, et al. (1991) "Pattern of morbidity and mortality in typhoid fever dependent on age and gender: review of 552 hospitalized patients with diarrhea," Rev. Infect. Dis. 13:85-90.

Cameron and Fuls (1976) "Immunizaion of mice and calves agaisnt *Salmonella dublin* with attenuated live and inactivated vaccines," J. Vet. Res. 43:31-38.

Cancellieri and Fara (1985) "Demonstration of specific IgA in human feces after immunization with live Ty21a *Salmonella typhi* vaccine," J. Infect. Dis. 151:482-484.

Caro, et al. (1999) "Physiological changes of *Salmonella typhimurium* cells under osomotic and starvation conditions by image analysis," FEMS Microbiol. Lett. 179:265-273.

Carrier, et al. (1992) "Expression of Human IL-1β in *Salmonella typhimurium*, a model system for the delivery of recombinant therapeutic proteins in vivo," J. Immunol. 148:176-181.

Carter and Collins (1974) "Growth of typhoid and paratyphoid Bacilli in travenously infected mice," Infect. Immun. 10:816-822.

Casadevall (1998) "Antibody-mediated protection against intracellular pathogens," Trends in Microbiol. 6:102-107.

Chabalgoity et al. (1995) "Influence of preimmunization with tetanus toxioid on immune responses to tetanus toxin fragment c-guest antigen fusions in *Salmonella* vaccine carrier," Infect. Immun. 63:2564-2569.

Chabalgoity et al. (1997) "Expression and immunogenicity of an *Echinococcus granulosus* fatty acid-binding protein in live attenuated *Salmonella* vaccine strains," Infect. Immun. 65;2402-2412.

Charles et al. (1990) "Isolation, characterization and nucleotide sequences of the *aroC* genes encoding chorismate synthase from *Salmonella typhi* and *Escherichia coli*," J. Gen. Microbiol. 136:353-358.

Chatfield, et al. (1992) "Use of the *nirB* promoter to direct the stable expression of heterologous antigens in *Salmonella* oral vaccine strains: development of a single-dose oral tetanus vaccine," Biotechnol. 10:888-892.

Chatfield, et al. (1992) "Evaluation of *Salmonella typhimurium* strains harbouring defined mutations in *htrA* and *aroA* in the murine salmonelloisis model," Microbial Pathog. 12:145-151.

Chatfield, et al. (1994) "Progress in Development of Mutlivalent Oral Vaccines Based on Live Attenuated *Salmonella*" in *Modern Vaccinolou* E. Kurstak, ed., Plenum Medical, New York, NY. 55-85.

Chen and Schifferli (2001) "Enhanced immune responses to viral epitopes by combining macrophage-inducible expression with multimeric display on a *Salmonella* vector," Vaccine, 19:3009-3018.

Chen, et al (1996) "Salmonella spp. are cytotoxic for cultured macrophages," Mol. Microbiol. 21:1101-1115.

Chuttani, et al. (1973) "Ineffectiveness of an oral killed typhoid vaccine in a field trial," Bull. Org. Mond. Sante, 48:756-757.

Chuttani, et al. (1977) "Controlled field trial of a high-dose oral killed typhoid vaccine in India," WHO 55:643-644.

Ciacci-Woolwine et al. (1997) "Salmonellae activate tumor necrosis factor apha production in a human promonocytic cell line via a released polypeptide," Infect. Immun. 65:4624-4633.

Cieslak et al. (1993) "Expression of a recombinant *Entamoeba histolytica* antigen in a *Salmonella typhimurium* vaccine strain," Vaccine 11:773-776.

Clairmont et al. (2000) "Biodistribution and genetic stability of the novel antitumor agent VPN20009, a genetically modified strain of *Salmonella typhimurium*" J. Infect. Dis. 181:1996-2002.

Clark, et al. (1996) "Invasion of murine intestinal M cells by *Salmonella typhimurium inv* mutants severely deficient for invasion of cultured cells," Infect. Immun. 64:4363-4368.

Clark, et al. (1998) "Inoculum composition and *Salmonella* pathogenicity island 1 regulate M-cell invasion and epithelial destruction by *Salmonella typhimurium*," Infect. Immun. 66:724-731.

Clements and El-Morshidy (1984) "Construction of a potential live oral bivalent vaccine for typhoid fever and cholera-*Escherichia coli*-Related diarrheas," Infect. Immun. 46:564-569.

Clements et al. (1986) "Oral immunization of mice with attenuated *Salmonella enteritidis* containing a recombinant plasmid which codes for production of the B subunit of heat-labile *Escherichia coli* enterotoxin," Infect. Immun. 53:685-692.

Cobelens, et al. (2000) "Typhoid fever in groups of travelers: Opporotunity for studying vaccine efficacy," J. Travel Med. 7:19-24.

Collins and Carter (1972) "Comparative immunogenicity of heat-killed and living oral *Salmonella* vaccines," Infect. Immun. 6:451-458.

Collins (1972) "Salmonellosis in orally infected specific pathogen-free C57B1 mice," Infect. lmmun. 5:191-198.

Cooper et al. (1992) "Vaccination of chickens with chicken-derived *Salmonella enteritidis* phage type 4 *aroA* live oral salmonella vaccines," Vaccine 10:247-254.

Corbel (1996) "Reasons for instablitiy of bacterial vaccines," Dev. Biol. Stand. 87:113-124.

Coulson et al. (1994) "*Bacillus anthracis* protective antigen, expressed in *Salmonella typhimurium* SL 3261, affords protection against anthrax spore challenge," Vaccine, 12:1395-1401.

Coulson et al. (1994) "Effect of different plasmids on colonization of mouse tissues by the aromatic amino acid dependent *Salmonella typhimurium*, SL 3261," Microbial Pathog. 16:305-311.

Coynault and Noral (1999) "Comparison of the abilities of *Salmonella typhimurium rpoS*, *aroA* and *rpoS aroA* strains to elicit humor immune responses in BALB/c mice to cause lethal infection in athymic BALB/c mice," Microbial Pathog. 26:299-305.

Coynault et al. (1996) "Virulence and vaccine potential of *Salmonella typhimurium* mutants deficient in the expression of the RpoS $\sigma^s$) regulon," Mol. Microbiol. 22:149-160.

Cryz et al. (1989) "Construction and characterization of a Vi-positive variant of the *Salmonella typhi* live oral vaccine strain Ty21a," Infect. Immun. 57:3863-3868.

Cryz et al. (1995) "Safety and immunogenicity of a live oral bivalent typhoid fever (*Salmonella typhi* Ty21a)-cholera (*Vibrio cholerae* CVD 103-HgR) vaccine in healthy adults," Infect. Immun. 63:1336-1339.

Curtiss and Kelly (1987) "*Salmonella typhimurium* deletion mutants lacking adenylate cyclase and cyclic AMP receptor protein are avirulent and immunogenic," Infect. Immun. 55:3035-3043.

Curtiss et al. (1989) "Recombinant avirulent Salmonella vaccine strains with stable maintenance and high level expression of cloned genes in vivo," Immunol. Invest. 18:583-596.

D'Amelio et al. (1988) "Comparative analysis of immunological responses to oral (Ty21a) and parenteral (TAB) typhoid vaccines," Infect. Immun.. 56:2731-2735.

De Almeida (1999) "Antibody responses against flagellin in mice orally immunized with attenuated *Salmonella* vaccine strains," Arch. Microbiol. 172:102-108.

Dham and Thompson (1982) "Studies of cellular and humoral immunity in typhoid fever and TAB vaccinated subjects," Clin. Exp. Immunol. 48:389-395.

Dilts, et al. (2000) "Phase I clinical trials of *aroA aroD* and *aroA aroD htrA* attenuated *S. typhi* vaccines; effect of formulation on safety and immunogenicity," Vaccine, 18:1473-1484.

Dima (1981) "Isolation and characterization of two *Salmonella typhosa* mutants for possible use as a live oral attenuated vaccinal strains," Arch. Roum. Path. Exp. Microbiol. 40:33-40.

Depetrillo (2000) "Safety and immunogenicity of PhoP/PhoQ-deleted *Salmonella typhi* expressing *Helicobacter pylori* urease in adult volunteers," Vaccine 18:449-459.

Djavani et al, (2001) "Mucosal immunization with *Salmonella typhimurium* expressing Lassa virus nucleocapsid protein cross-protects mice from lethal challenge with lymphocytic choriomeningitis virus," J. Hum. Virol. 4:103-108.

Dorman et al. (1989) "Characterization of porin and *ompR* mutants of a virulent strain of *Salmonella typhimurium*: *ompR* mutants are attenuated in vivo," Infect. Immun. 57:2136-2140.

Dorner (1995) "An overview of vaccine vectors," Dev. Biol. Stand. 84:23-32.

Douce, et al. (1991) "Invasion of HEp-2 cells by strains of *Salmonella typhimurium* different virulence in relation to gastroenteritis," J. Med. Microbiol. 35:349-357.

Dougan, et al. (1988) "Construction and characterization of vaccine strains of *Salmonella* harboring mutations in two different *aro* genes," J. Infect. Dis. 158:1329-1335.

Dragunsky et al. (1990) "In vitro characterization of *Salmonella typhi* mutant strains for live oral vaccines," Vaccine 8:263-268.

Dragunski et al. (1989) "*Salmonella typhi* vaccine strain in vitro; low inefectivity in human cell line U937," J. Biol. Stand. 17:353-360.

Dunstan et al. (1999) "Use of in vivo-regulated promoters to deliver antigens from attenuated *Salmonella enterica* var. Typhimurium," Infect. Immun. 67:5133-5141.

Dupont et al. (1971) "Studies of immunity in typhoid fever," Bull. Org. Mond. Sante. 44:667-672.

Edwards and Stocker (1988) "Construction of $\Delta aroA$ his $\Delta pur$ strains of *Salmonella typhi*," J. Bacteriol. 170:3991-3995.

Eichelberg and Galan (1999) "Differential regulation of *Salmonella typhimurium* type III secreted proteins by pathogenicity island I (SPI-1)-encoded transcriptional activators InvF and HilA," Infect. Immun. 67:4099-4105.

Emmerth, et al. (1999) "Genomici subtraction identifies *Salmonella typhimurium* prophages, F-related plasmid sequences, and a novel fimbrial operon, stf, which are absent in *Salmonella typhi*," J. Bacteriol. 181:5652-5661.

Engels, et al. (1998) "Typhoid fever vaccines: a meta-analysis of studies on efficacy and toxicity," BMJ, 316:110-113.
Everest, et al. (1999) "Evaluation of *Salmonella typhimurizim* Mutants in a model of experimental gastroenteritis," Infect. Immun. 67:2815-2821.
Fallon, et al. (1991) "Mouse hepatitis virus strain UAB infection enhances resistence to *Salmonella typhimurium* in mice by inducing supression of bacterial growth," Infect. Immun. 59:852-856.
Ferricio (1989) "Comparative efficacy of two, three or four doses of TY21a live oral vaccine in enteric coated capsules: a field trial in an endemic area," J. Infect. Dis. 159:766-769.
Finlay and Falkow (1997) "Common themes in microbial pathogenicity revisited," Microbiol. Mol. Biol. Rev. 61:136-169.
Formal et al. (1981) "Construction of a potential bivalent vaccine strain: introduction of *Shigella sonnei* form I antigen genes into the galE *Salmonella typhi* Ty21a typhoid vaccine strain," Infect. Immun. 34:746-750.
Forrest and LaBrooy (1993) "Effect of parenteral immunization on intestinal immune response to *Salmonella typhi* Ty21a as measured using peripheral blood lymphocytes," Vaccine, 11:136-139.
Fu and Galan (1998) "The *Salmonella typhimurium* tyrosine phosphatase SptP is translocated into host cells and disrupts the actin cytoskeleton," Mol. Microbiol. 27:359-368.
Gahring, et al. (1990) "Invasion and replication of *Salmonella typhimurium* in animal cells," Infect. Immun. 58:443-448.
Galan and Colimer (1999) "Type III secretion machines: bacterial devices for protein delivery into host cells," Science, 284:1322-1328.
Galan and Zhou (2000) Striking a balance: modulation of the actin cytoskeleton by *Salmonella*. PNAS, 97:8754-8761.
Galan, et al (1990) "Cloning and characterization of the *asd* gene of *Salmonella typhimurium*: use in a stable maintenance of recombinant plasmids in *Salmonella* vaccine strains," Gene, 94:29-35.
Galan and Levine (2001) "Can a 'flawless' love vector strain be engineered?" Trends in Microbiol. 9:372-376.
Galan (1996) "Molecular genetic bases of *Salmonella* entry into host cells," Mol. Microbiol. 20:263-271.
Galen et al. (1999) "Optimization of plasmid maintenance in attenuated live vector vaccine strain *Salmonella typhi* CVD 908-*htrA*" Infect. Immun. 67:6424-6433.
Garcia-Del Portillo, et al. (1993) "*Salmonella* induces the formation of filament structures containing lysosomal membrane glycoproteins in epithelial cells," PNAS, 90:10544-10548.
Garmory et al. (2002) "*Salmonella* vaccines for use in humans: present and future perspectives," FEMS Microbiol. Rev. 26:339-353.
Gautier et al. (1998) "Mouse susceptibility to infection by the *Salmonella abortusovus* vaccine strain Rv6 is controlled by the Ity/Nramp 1 gene and influences the antibody response but not the complement response," Microbial Pathog. 24:47-55.
Gentschev et al. (2000) "Delivery of protein antigens and DNA by virulence attenuated strains of *Salmonella typhimurium* ans *Listeria monocytogenes*," J. Bacteriol. 83:19-26.
Germanier and Furer (1975) "Isolation and characterization of *Gal E* mutant Ty21a of *Salmonella typhi*: a candidate strain for a live oral typhoid vaccine," J. Infect. Dis. 131:553-558.
Germanier and Levine (1986) "The live typhoid vaccine Ty21a: recent field trial results," Bacterial Vaccines and Local Immunity:19-22.
Gewirtz et al (1999) "Orchestration of neutrophil movement by intestinal epithelial cells in response to *Salmonella typhimurium* can be uncoupled from bacterial internalization," Infect. Immun. 67:608-617.
Gilman (1977) "Evaluation of UDP-glucose-4-epineraseless mutant of *Salmonella typhi* as a live oral vaccine," J. Infect. Dis. 130:717-723.
Giron et al. (1995) "Simultaneous expression of CFA/I and CS3 colonization factor antigens of enterotoxifenic *Escherichia coli* by ΔaroC, ΔaroD *Salmonella typhi* vaccine strain CVD 908," Vaccine, 13:939-946.
Gonzales, et al. (1994) "*Salmonella typhi* vaccine strain CVD 908 expressing the circumsporozoite protein of *Plasmodium faliciparum*: Strain construction and safety and immunogenicity in humans," J. Infect. Dis. 169:927-931.

Gonzales et al. (1998) "Immunogenicity of a *Salmonella typhi* CVD 908 candidate vaccine strain expressing the major surface protein gp63 of *Leishmania mexicana mexicana*," Vaccine 16:1043-1052.
Grossman et al. (1995) "Flagellar serotypes of *Salmonella typhi* in Indonesia: Relatioships among motility, invasiveness, and clinical illness" J. Infect. Dis. 171:212-216.
Guard-Petter, et al. (1995) "Characterization of lipopolysaccharide heterogeneity in *Salmonella enteritidis* by an improved gel electrophoresis method," Appl. Eviron. Microbiol., 61;2845-2851.
Guerrant and Kosek (2001) "Polysaccharide conjugate typhoid vaccine," NEJM, 344:1322-1323.
Guillobel et al. (2000) "Adjuvant activity of a nontoxic mutant *Eschericia coli* heat-labile enterotoxin on systemic and mucosal immune responses elicited against a heterologous antigen carried by a live *Salmonella entericai* serovar typhimurium vaccine strain," 68:4349-4353.
Gunn et al. (1995) "Characterization of the *Salmonella typhimurium pagC/pagD* Chromosomal region," J. Bacteriol. 177:5040-5047.
Guo et al. (1997) "Regulation of lipid modifications by *Salmonella typhimurium* virulence genes *phoP-phoQ*," Science, 276:250-253.
Hacket (1993) "Use of *Salmonella* for heterologous gene expression and vaccine delivery systems," Curr. Opin. Biotechnol. 4:611-615.
Hall and Taylor (1970) "Salmonella Dublin: The relation between a living calf vaccine strain and those isolated from human and other sources," Vet. Rec. 86:534-536.
Harrison et al. (1997) "Correlates of protection induced by live Aro' *Salmonella typhimurium* vaccines in the murine typhoid model," lmmunol. 90:618-625.
Herrington et al. (1990) "Studies in volunteers to evaluate candidate *Shigella* vaccines: further experience with a bivalent *Salmonella typhi-Shigella sonnei* vaccine and protection conferred by previous *Shigella sonnei* disease," Vaccine, 8:353-357.
Hess et al. (1996) "*Salmonella typhimurium* aroA infection in gene-targeted immunodeficient mice; major role of $CD4^+$ TCR-$\alpha\beta$ cells in IFN-$\gamma$ in bacterial clearance independent of intracellular location," J. Immunol. 156:3321-3326.
Hindle et al. (2002) "Characterization of *Salmonella enterica* derivatives harboring defined *aroC* and *Salmonella* pathogenicity island 2 type III secretion system (*ssaV*) mutaions by immunization of healthy volunteers," Infect. Immun. 70:3457-3467.
Hirose et al. (1997) "Survival of Vi-capsulated and Vi-deleted *Salmonella typhi* strains in cultured macrophage expressing different levles of CD14 antigen," FEMS Microbiol. Lett. 147:259-265.
Hohmann and Oletta (1996) "*phoP/phoQ*- deleted *Salmonella typhi* (Ty800) is safe and immunogenic single-dose fever vaccine in volunteers," J. Infect. Dis. 173:1408-1414.
Hoisth and Stocker (1981) "Aromatic-dependent *Salmonella typhimurium* are non-virulent and effective as live vaccines," Nature, 291:238-239.
Holden (2002) "Trafficking of the *Salmonella* vacuole in macrophages," Traffic, 3:1-11.
Holmstrom, et al. (1999) "Physiological states of individual *Salmonella typhimurium* cells monitored by in situreverse transcription PCR," J. Bacteriol. 181:1733-1738.
Hone et al. (1988) "A *galE* via (Vi antigen-negative) mutant *Salmonella typhi* Ty2 retains virulence in humans," Infect. Immun. 56:1326-1333.
Hone et al (1991) "Construction of genetically defined double aro mutants of *Salmonella typhi*," Vaccine, 9:810-816.
Hone et al. (1992) "Evaluation in volunteers of candidate live oral attenuated *Salmonella typhi* vector vaccine," J. Clin. Invest. 90:412-420.
Hone, et al. (1994) "Adaptive acid tolerance response by *Salmonella typhi* and candidate live oral typhoid vaccine strains," Vaccine, 12:895-898.
Hopkins, et al. (1995) "A recombinant *Salmonella typhimurium* vaccine induces local immunity by four different routes of immunization," Infect. Immun. 63:3279-3286.
Hormaeche (1979) "Natural resistance to *Salmonella typhimurium* in different inbred mouse strains," Immunol. 37:311-318.
Hornick (1970) "Typhoid fever: pathogenesis and immunogic control," NEJM, 283: 739-742.

House, et al. (2001) "Typhoid fever: pathogenesis and disease," Curr. Opin. Infect. Dis. 14:573-578.

Humphreys, et al. (1999) The alternative sigma factor, $\sigma^E$ is critically important for the virulence of *Salmonella typhimurium*, Infect. Immun. 67:1560-1568.

Ishibashi and Arai (1995) "*Salmonella typhi* does not inhibit phagosome-lysosome fusion n human monocyte derived macrophages," FEMS Immunol. Med. Microbiol. 12:55-62.

Jepson et al. (1996) "Evidence for a rapid, direct effect on epithelial monolayer integrity and transepithelial transport in response to *Salmonella* invasion," Eur. J. Physiol. 432:225-233.

Johnston et al. (1996) "Transcriptional activation of *Salmonella typhimurium* invasion genes by a member of the phosphorylated response-regulator superfamily," Mol. Microbiol. 22:715-727.

Jones et al. (1981) "The invasion of HeLa cells by *Salmonella typhimurium*: Reversible and irreversable bacterial attachment and the role of bacterial motility," J. Gen. Microbiol. 127:351-360.

Kantele, et al. (1991) "Comparision o the human immune response to live oral, killed oral or killed parenteral *Salmonella typhi* Ty21A vaccines," Microbial Pathog. 10:117-126.

Kantele et al. (1998) "Differences in immune responses induced by oral and rectal immunizations with *Salmonella typhi* TY21a: Evidence for compartmentalization within the common mucosal immune system in humans," Infect. Immun. 66:5630-5635.

Karem, et al. (1995) "Differential induction of carrier antigen-specific immunity by *Salmonella typhimurium* live-vaccine strains after single mucosal or intravenous immunization of Balb/c mice," Infect. Immun. 63:4557-4563.

Karem, et al. (1997) "Protective immunity against herpes simplex (HSV) type 1 following oral administration of recombinant *Salmonella typhimurium* vaccine strains expressing HSV antigens," J. Gen. Virol. 78:427-434.

Kaufman and Hess (1999) "Impact of intracellular location of and antigen display by intracellular bacteria: implications for vaccine development," Immunol. Lett. 65:81-84.

Kawakami, et al. (1969) "Experimental Salmonellosis immunizing effect of live vaccine prepared from various mutants of *Salmonella* having different cell wall polysaccharides," Japan. J. Microbiol. 13:315-324.

Keddy, et al. (1998) "Efficacy of Vi polysaccharide vaccine against strains of *Salmonella typhi*: reply" Vaccine, 16:871-872.

Kehres, et al. (2000) "The NRAMP proteins of *Salmonella typhimurium* and *Escherichia coli* are selective manganese transporters involved in the response to reactive oxygen," Mol. Microbiol. 36:1085-1100.

Keitel, et al. (1994) "Clinical and serological responses following primary and booster immunizations with *Salmonella typhi* Vi capsular polysaccharicde vaccines," 12:195-199.

Kelly, et al. (1992) "Characterization and protective properties of attenuated mutants of *Salmonella choleraesuis*," Infect. Immun. 60:4881-4890.

Keren, et al. (1978) "The role of peyer's patches in the local immune response of rabbit ileum to live bacteria," J. Immunol. 120:1892-1896.

Khan, et al. (1998) "*Salmonella typhi rpoS* mutant is less cytotoxic than the parent strain but survives inside resting THP-1 macrophages," FEMS Microbiol. Lett. 161:201-208.

Khan et al. (1998) "A lethal role for lipid A in *Salmonella* infections," Mol. Microbiol. 29:571-579.

Khan et al. (2001) "Early responses to *Salmonella typhimurium* infection in mice occur at focal lesions in infected organs," Microbial Pathog. 30:29-38.

Khan et al. (2003) "*Salmonella typhi* and *S. typhimurium* derivatives harbouring deletions in aromatic biosynthesis and *Salmonella* pathogenicity island-2 (SPI-2) genes as vaccines and vectors," Vaccine, 21:538-548.

Khan, et al. (2007) "Ability of SPI2 mutant of *S. tyhpi* to effectively induce antibody responses to the mucosal antigen enterotoxigenic *E. coli* heat labile toxin B subunit after oral delivery to humans," Vaccine, 25:4175-4182.

Kingsley and Baumler (2000) "Host adaptation and the emergency of infectious disase: the *Salmonella* paradigm," 1006-1014.

Kirkpatrick, et al. (2005) "Comparison of the antibodies in lymphocyte supernatant and antibody-secreting cells assays for measuring intestinal mucosal immune response toa novel oral typhoid vaccine (M01ZH09)" Clin. Diagnostic Lab. lmmunol. 12:1127-1129.

Kirkpatrick et al. (2005) "The novel oral typhoic vaccine M01ZH09 is well tolerated and highly immunogenic in 2 vaccine presentations," J. Infect. Dis. 192:360-366.

Kirkpatrick, et al. (2006) "Evaluation of *Salmonella enterica* serovar Typhi (Ty2 *aroC-ssaV*- ) M01ZH09, with a defined mutation in the *Salmonella* pathogenicity island 2, as a live, oral typhoic vaccine in human volunteers," Vaccine, 24:116-123.

Klugman, et al. ( 1987) "Protease activity of Vi capsular polysaccharide vaccine against typhoid fever," Lancet, 1165-1169.

Kohbata, et al. (1986) "Cytopathogenic effect of *Salmonella typhi* GIFU 10007 on M cells of murine ileal peyer's patches in ligated ileal loops: an ultrastructural study," Microbiol. Immunol. 30:1225-1237.

Kohler et al., (2000) "Effect of preexisting immunity to *Salmonella* on the immune response to recombinant *Salmonella enterica* serovar typhimurium expressing a *Porphyromonas gingivalis* hemagglutinin," Infect. Immun. 68:3116-3120.

Kollaritsch et al. (1996) "Randomized double-blind placebo-controlled trial to evaluate the safety and immunogenicity of combined *Salmonella typhi* Ty2la and *Vibrio cholerae* CVD 103-HgR live oral vaccines," Infect. Immun. 64:1454-1457.

Kollaritsch et al. (1997) "Safety and immunogenicity of live oral Cholera and Typhoid vaccines administered alone or in combination with antimalarial drugs, oral polio vaccines, or yellow fever vaccine," J. Infect. Dis. 871-875.

Kollaritsch, et al. (2000) "Local and systemic immune responses to combined *Vibrio cholerae* CVD103-HgR and *Salmonella typhi* Ty2la live oral vaccines after primary immunization and reimmunization," Vaccine 18:3031-3039.

Kotloff, et al. (1996) "Safety, immunogenicity, and transmissibility in humans in CVD 1203 a live oral *Shigella flexneri* 2a vaccine candidate attenuated by deletions in *aroA* and *virG*," Infect. Immun. 64:4542-4548.

Kramer and Vote (2000) "Granulocyte selected live *Salmonella enteritidis* vaccine is species specific," Vaccine, 18:2239-2243.

Lalmanach and Lantier (1999) "Host cytokine response and resistance to *Salmonella* infection," Microbes Infect. 1:719-726.

Lebacq (2001) "Comparative tolerability an immunogenicity of Typherix™ or Typhium Vi™ in healthy adults," Drugs, 15 Suppl. 1:5-12.

Leclerc, et al. (1998) "Environmental regulation of *Salmonella typhi* invasion-defective mutants," Infect. Immun. 66:682-691.

Lee and Schneewind (1999) "Type III secretion machines and the pathogenesis of enteric infections caused by *Yersina* and *Salmonella spp*." Immunol. Rev. 168:241-255.

Lee et al. (2000) "Surface-displayed viral antigens on *Salmonella* carrier vaccine," Nature Biotechnol. 18:645-648.

Lee et al. (2000) "OmpR regulates the two-component system SsrA-SsrB in *Salmonella* pathogenicity island 2," J. Bacteriol. 182:771-781.

Lehoux et al. (1999) "Defined oligonucleotide tag pools and PCR screeing in signature-tagged mutagenesis of essential genes from bacteri," BioTechniques 26:473-480.

Leung and Finlay (1991) "Intracellular replication is essential for the virulence of *Salmonella typhimurium*," PNAS 88:11470-11474.

Levine and Sztein (1996) "Human mucosal vaccines for *Salmonella typhi* infections," in *Mucosal Vaccines*, Kiyono, et al., eds. Academic Press, San Diego.

Levine, et al. (1985) "The efficacy of attenuated *Salmonella typhi* oral vaccine strain Ty2Ia evaluated in controlled field trials," Dev.Vaccines and Drugs agains diarrhea, 11th nobel Conf. Stockholm, pp. 90-101.

Levine et al. (1987) "Safety, infectivity, immunogenicity, and in vivo stability of two attenuated auxotrophic mutant strains of *Salmonella typhi*, 541Ty and 543Ty, as live oral vaccines in human," J. Clin. Invest. 79:888-902.

Levine (1987) "Large-scale field trial of Ty21a live oral typhoid vaccine in enteric-coated capsule formulation." Lancet, 1049-1052.

Levine et al. (1989) "Progress in vaccines against typhoid fever," Rev. Infect. Dis. 11:S552-S567.

Levine, et al. (1990) "Comparison of enteric-coated capsules and liquid formulation of Ty2la typhoid vaccine in randomised comtrolled field trial," Lancet, 336:891-894.

Levine et al. (1997) "Attenuated *Salmonella typhi* and *Shigella* as love oral vaccines and as live vectors," Behring Inst. Mitt. 98:120-123.

Levine, (1994) "Typhoid Fever Vaccines," in *Vaccines*, Plotkin and Mortimer, eds., W.B. Saunders Company, Philadelphia, 597-633.

Levine, et al. (1999) "Duration of efficacy of Ty2la, attenuated *Salmonella typhi* live oral vaccine," Vaccine, 17:S22-S27.

Levine, et al. (1997) "Attenuated Salmonella as a live vector for expression of foreign antigens. Part iii. Salmonella expressing protozoal antigens," in *New Generation Vaccines $2^{nd}$* ed., Levine, et al., eds. Marcel Dekker, New York. 351-361.

Levine et al. (2001) "Host-Salmonella interaction: human trials," Microbes Infect. 3:1271-1279.

Liang-Takasaki, et al. (1982) "Phagocytosis of bacteria by macrophages: Changing the carbohydrate of lipopolysaccharide alters interatction with complement, and macrophages," J. Immunol. 128:1229-1235.

Liang-Takasaki et al. (1983) "Complement activation by polysaccharide of lipopolysaccharide: an important virulence determinant of *Salmonellae*," Infect. Immun. 41:563-569.

Liang-Takasaki, et al. (1983) "Salmonellae activate complement differentially via the alternative pathway depending on the structure of their lipopolysaccharide O-antigen," J. Immunol. 130:1867-1870.

Libby et al. (1994) "A cytolysin encoded by *Salmonella* is required for survival within macrophages," PNAS, 91:489-493.

Liu, (1988) "Intact motility as *Salmonella typhi* invasion-related factor," Infect. Immun. 56:1967-1973.

Lodge, et al. (1995) "Biological and genetic characterization of Tn*phoA* mutants of *Salmonella typhimurium* TML in the context of gastroenteritis," Infect. Immun. 63:762-769.

Londono et al. (1995) "Immunization of mice using *Salmonella typhimurium* expressing human papillomavirus type 16 E7 epitopes inserted into hepatitis B virus core antigen," Vaccine, 14:545-552.

Low, et al. (1999) "Lipid A mutant *Salmonella* with suppressed virulence and TNFα induction retain tumor-targeting in vivo," Nature Biotechnol. 17:37-41.

Lucas, et al. (2000) "Unravelling the mysteries of virulence gene regulation in *Salmonella typhimurium*," Mol. Microbiol. 36:1024-1033.

Lundberg, et al. (1999) "Growth phase-regulated induction of *Salmonella*-induced macrophage apoptosis correlates with transient expression of SPI-1 genes," J. Bacteriol. 181:3433-3437.

Marshall, et al. (2000) "Use of the stationary phase inducible promoters, spv and dps, to drive heterologous antigen expression in Salmonella vaccine strains," Vaccine 18: 1298-1306.

Mastroeni, et al. (1998) "Interleukin-12 Is Required for Control of the Growth of Attenuated Aromatic-Compound-Dependent *Salmonellae* in BALB/c Mice: Role of Gamma Interferon and Macrophage Activation," Infect. Immun. 66: 4767-4776.

Mastroeni, et al. (1995) "Effect of Anti-Tumor Necrosis Factor Alpha Antibodies on Histopathology of Primary Salmonella Infections," Infect. Immun. 63: 3674-3682.

Mastroeni, et al. (1992) "Role of T cells, TNFα and IFNγ in recall of immunity to oral challenge with virulent *salmonellae* in mice vaccinated with live attenuated aro- salmonella vaccines," Microbial Pathogen. 13: 477-491.

Mazurkiewicz, et al. (2006) "Signature-tagged mutagenesis: barcoding mutants for genome-wide screens," Nat. Rev. Genet. 7: 929-939.

Mcfarland and Stocker (1987) "Effect of different purine auxotrophic mutations on mouse-virulence of a Vi-positive strain of *Salmonella* dubl in and of two strains of *Salmonella typhimurium*," Microbial Pathogen. 3: 129-141.

Mcsorley and Jenkins (2000) "Antibody Is Required for Protection against Virulent bu Not Attenuated *Salmonella enterica* Serovar *Typhimurium*," Infect. Immun. 68: 3344-3348.

Medina and Guzman (2001) "Use of live bacterial vaccine vectors for antigen delivery: potential and limitations," Vaccine 19: 1573-1580.

Miao and Miller (2000) "A conserved amino acid sequence directing intracellular type II secretion by *Salmonella typhimuirim*," Proc. Natl. Acad. Sci. USA 97: 7539-7544.

Mills and Finlay (1994) "Comparison of *Salmonella typhi* and *Salmonella typhimurim* invasion, intracellular growth and localization in cultured human epithelial. cells," Microbial. Pathogen. 17: 409-423.

Mills, et al. (1998) "Trafficking of Porin-Deficient *Salmonella typhimurium* Mutants inside HeLa Cells: ompR and envZ Mutants Are Defective for the Formation of *Salmonella*-Induced Filaments," Infect. Immun. 66: 1806-1811.

Mintz, et al. (1983) "Effect of Lipopolysaccharide Mutations on the Pathogenesis of Experimental *Salmonella* Gastroenteritis," Infect. Immun. 40: 236-244.

Mittrücker and Kaufmann (2000) "Immune response to infection with *Salmonella typhimurium* in mice," J. Leukoc. Biol. 67: 457-463.

Mittrücker, et al. (2000) "Cutting Edge: Role of B Lymphocytes in Protective Immunity Against *Salmonella typhimurium* Infection," J. Immunol 164: 1648-1652.

Mollenkopf, et al. (2001) "Protective efficacy against tuberculosis of ESAT-6 secreted by a live *Salmonella typhimurium* vaccine carrier strain and expressed by naked DNA," Vaccine 19: 4028-4035.

Mollenkopf, et al. (2001) "Intracellular Bacteria as Targets and Carriers for Vaccination," Biol. Chem. 382: 521-532.

Nardelli-Haefliger, et al. (2001) "Nasal vaccination with attenuated *Salmonella typhimurium* strains expressing the Hepatitis B nucleocapsid: dose response analysis," Vaccine 19: 2854-2861.

Nardelli-Haefliger, et al. (1996) "Oral and Rectal Immunization of Adult Female Volunteers with a Recombinant Attenuated *Salmonella typhi* Vaccine Strain," Infect. Immun. 64: 5219-5224.

Nauciel and Espinasse-Maes (1992) "Role of Gamma Interferon and Tumor Necrosis Factor Alpha in Resistance to *Salmonella typhimurium* Infection," Infect. Immun. 60: 450-454.

Nauciel (1990) "Role of CD4+ T Cells and T-Independent Mechanisms in Acquired Resistance to *Salmonella typhimurium* Infection," J. Immunol. 145: 1265-1269.

Nickerson and Curtiss III, et al. (1997) "Role of Sigma Factor RpoS," in Initial Stages of *Salmonella typhimurium* Infection, Infect. Immun. 65: 1814-1823.

Ornellas, et al. (1970) "The Specificity and Importance of Humoral Antibody in the Protection of Mice against Intraperitoneal Challenge with Complement-Sensistive and Complement-Resistant Salmonella," J. Infect. Disease 121: 113-123.

Paesold, et al. (2002) "Genes in the *Salmonella* pathogenicity island 2 and the Salmonella virulence plasmid are essential for *Salmonella*-induced apoptosis in intestinal epithelial cells," Cell. Microbiol. 4: 771-781.

Paglia, et al. (2000) "In vivo correction of genetic defects of monocyte/macrophages using attenuated *Salmonella* as oral vectors for targeted gene delivery," Gene Therapy 7: 1725-1730.

Pang, et al. (1995) "Typhoid fever and other salmonellosis: a continuing challenge," Trends Microbiol. 3: 253-255.

Pickard, et al. (1994) "Characterization of Defined ompR Mutants of *Salmonella typhi*: ompR Is Involved in the Regulation of Vi Polysaccharide Expression," Infect. Immun. 62: 3984-3993.

Pickett, et al. (2000) "In Vivo Characterization of the Murine Intranasal Model for Assessing the Immunogenicity of Attenuated *Salmonella enterica* Serovar Typhi Strains as Live Mucosal Vaccines and as Live Vectors," Infect. Immun. 68: 205-213.

Pie, et al. (1997) "Th1 Response in *Salmonella typhimurium*-Infected Mice with a High or Low Rate of Bacterial Clearance," Infect. Immun. 65: 4509-4514.

Pier, et al. (1998) "*Salmonella typhi* uses CFTR to enter intestinal epithelial cells," Nature 393: 79-82.

Poirer, et al. (1988) "Protective Immunity Evoked by Oral Administration of Attenuated aroA *Salmonella typhimurium* Expressing Cloned Streptococcal M Protein," J. Exp. Med. 168: 25-32.

Pulkkinen and Miller (1991) "A *Salmonella typhimurium* Virulence Protein Is Similar to a *Yersinia enterocolitica* Invasion Protein and a Bacteriophage Lambda Outer Membrane Protein," J. Bacteriol. 173: 86-93.

Qian and Pan (2002) "Construction of a tetR-Integrated *Salmonella enterica* Serovar Typhi CVD908 Strain That Tightly Controls Expression of the Major Merozoite Surface Protein of *Plasmodium falciparum* for Applications in Human Vaccine Production," Infect. Immun. 70: 2029-2038.

Rakeman, et al. (1999) "A HiIA-Independent Pathway to *Salmonella typhimurium* Invasion Gene Transcription," J. Bacteriol. 181: 3096-3104.

Richter-Dahlfors, et al. (1997) "Murine Salmonollosis Studied by Confocal Microscopy: *Salmonella typhimurium* Resides Intracellularly Inside Macrophages and Exerts a Cytotoxic Effect on Phagocytes In Vivo," J. Exp. Med. 186: 569-580.

Robbe-Saule, et al. (1995) "The live oral typhoid vaccine Ty2la is a rpoS mutant and is susceptible to various environmental stresses," FEMS Microbiol. Lett. 126: 171-176.

Roberts, et al. (2000) "Comparison of Abilities of *Salmonella enterica* Serovar Typhimurium aroA aroD and aroA htrA Mutants To Act as Live Vectors," Infect. Immun. 68: 6041-6043.

Roberts, et al. (1999) "Prior Immunity to Homologous and Heterologous *Salmonella* Serotypes Suppresses Local and Systemic Anti-Fragment C Antibody Responses and Protection from Tetanus Toxin in Mice Immunized with *Salmonella* Strains Expressing Fragment C," Infect. Immun. 67: 3810-3815.

Roberts, et al. (1998) "Oral Vaccination against Tetanus: Comparison of the Immunogenicities of *Salmonella* Strains Expressing Fragment C from the nirB and htrA Promoters," Infect. Immun. 66: 3080-3087.

Roland, et al. (1999) "Construction and Evaluation of a Δcya Δcrp *Salmonella typhimurium* Strain Expressing Avian Pathogenic *Escherichia coli* O78 LPS as a Vaccine to Prevent Airsacculitis in Chickens," Avain Diseases 43: 429-441.

Schödel, et al. (1993) "Avirulent *Salmonella* expressing hybrid hepatitis B virus core/pre-S genes for oral vaccination," Vaccine 11: 143-148.

Schödel, et al. (1994) "Development of Recombinant *Salmonellae* Expressing Hybrid Hepatitis B Virus Core Particles as Candidate Oral Vaccines," Brown F(ed): Recombinant Vectors in Vaccine Development. Dev. Biol. Stand. Basel, Karger 82: 151-158.

Schwan, et al. (2000) "Differential Bacterial Survival, Replication, and Apoptosis-Inducing Ability of *Salmonella* Serovars within Human and Murine Macrophages," Infect. Immun. 68: 1005-1013.

Shata, et al. (2000) "Recent advances with recombinant bacterial vaccine vectors," Mol. Med. Today 6: 66-70.

Sinha, et al. (1997) "*Salmonella typhimurium* aroA, htrA, and aroD htrA Mutants Cause Progressive Infections in Athymic (nu/nu) BALB/c Mice," Infect. Immun. 65: 1566-1569.

Sirard, et al. (1999) "Live attenuated *Salmonella*: a paradigm of mucosal vaccines," Immunol. Rev. 171: 5-26.

Smith, et al. (1984) "Aromatic-dependent *Salmonella dublin* as a parenteral modified live vaccine for calves," Am. J. Vet. Res. 45: 2231-2235.

Smith, et al. (1993) "Vaccination of calves with orally administered aromatic-dependent *Salmonella dublin*," Am. J. Vet. Res. 54: 1249-1255.

Soo, et al. (1998) "Genetic Control of Immune Response to Recombinant Antigens Carried by an Attenuated *Salmonella typhhimurium* Vaccine Strain: Nrampl Influences T-Helper Subset Responses and Protection against Leishmanial Challenge," Infect. Immun. 66: 1910-1917.

Stein, et al. (1996) "Identification of a *Salmonella* virulence gene required for formation of filamentous structures containing lysosomal membrane glycoproteins within epithelial cells," Mol. Microbiol. 20: 151-164.

Stocker (2000) "Aromatic-dependent *Salmonella* as anti-bacterial vaccines and as presenters of heterologous antigens or of DNA encoding them," J. Biotechnol. 83: 45-50.

Stocker (1990) "Aromatic-Dependent *Salmonella* as Live Vaccine Presenters of Foreign Epitopes as Inserts in Flagellin," Res. Microbiol. 141: 787-796.

Stocker (1988) "Auxotrophic *Salmonella typhi* as live vaccine," Vaccine 6: 141-145.

Svenson and Lindberg (1983) "Artificial *Salmonella* Vaccines," Prog. Allergy 33: 120-143.

Sydenham, et al. (2000) "*Salmonella enterica* Serovar Typhimurium surA Mutants Are Attenuated and Effective Live Oral Vaccines," Infect. Immun. 68: 1109-1115.

Sztein, et al. (1994) "Cytokine Production Patterns and Lymphoproliferative Responses in Volunteers Orally Immunized with Attenuated Vaccine Strains of *Salmonella tyhpi*," J. Infect. Disease 170: 1508-1517.

Tacket, et al. (2000) "Phase 2 Clinical Trial of Attenuated *Salmonella enterica* Serovar Typhi Oral Live Vector Vaccine CVD 908-htrA in U.S. Volunteers," Infect. Immun. 68: 1196-1201.

Tacket, et al. (2000) "Safety and Immune Responses to Attenuated *Salmonella enterica* Serovar Typhi Oral Live Vector Vaccines Expressing Tetanus Toxin Fragment C," Clin. Immunol. 97: 146-153.

Tacket, et al. (1997) "Safety of Live Oral *Salmonella typhi* Vaccine Strains with Deletions in htrA and aroC aroD and Immune Response in Humans," Infect. Immun. 65: 452-456.

Tacket, et al. (1992) "Clinical acceptability and immunogenicity of CVD 908 *Salmonella typhi* vaccine strain," Vaccine 10: 443-446.

Tacket, et al. (1992) "Comparison of the Safety and Immunogenicity of ΔaroC ΔaroD and Δcya Δcrp *Salmonella typhi* Strains in Adult Volunteers," Infect. Immun. 60: 536-541.

Tacket, et al. (1991) "Lack of Immune response to the Vi Component of a Vi-Positive Variant of *Salmonella typhi* Live Oral Vaccine Strain Ty2Ia in Human Studies," J. Infect. Disease 163: 901-904.

Tacket, et al. (1988) "Persistence of antibody titres three years after vaccination with Vi polysaccharide vaccine against typhoid fever," Vaccine 6: 307-308.

Tacket, et al. (1986) "Safety and Immunogenicity of Two *Salmonella typhi* Vi Capsular Polysaccharide Vaccines," J. Infect. Disease 154: 342-345.

Tagliabue (1989) "Immune Response to Oral *Salmonella* Vaccines," Curr. Topics Microbiol. Immunol. 146: 225-231.

Tang, et al. (2001) "Identification of bacterial genes required for in-vivo survival," J. Pharm. Pharmacol. 53: 1575-1579.

Tite, et al. (1991) "The Involvement of Tumor Necrosis Factor in Immunity to *Salmonella* Infection," J. Immunol. 147: 3161-3164.

Tramont, et al. (1984) "Safety and Antigenicity of Typhoid-Shigella sonnei Vaccine (Strain 5076-1C)," J. Infect. Disease 149: 133-136.

Turner, et al. (1993) "*Salmonella typhimurium* ΔaroA ΔaroD Mutants Expressing a Foreign Recombinant Protein Induce Specific Major Histocompatibility Complex Class I-Restricted Cytotoxic T Lymphocytes in Mice," Infect. Immun. 61: 5374-5380.

Uchiya, et al. (1999) "A *Salmonella* virulence protein that inhibits cellular trafficking," EMBO J. 18: 3924-3933.

Urashima, et al. (2000) "An oral CD40 ligand gene therapy against lymhoma using attenuated *Salmonella typhimurium*," Blood 95: 1258-1263.

Valdivia and Falkow (1996) "Bacterial genetics by flow cytometry: rapid isolation of *Salmonella typhimurium* acid-inducible promoters by differential fluorescence induction," Mol. Microbiol. 22: 367-378.

Van Dissel, et al. (1995) "S. Typhi Vaccine Strain Ty2la Can Cause a Generalized Infection in Whole Body-Irradiated But Not in Hydrocortisone-Treated Mice," Scand. J. Immunol. 41: 457-461.

Van Velkinburgh and Gunn (1999) "PhoP-PhoQ-Regulated Loci Are Required for Enhanced Bile Resistance in Salmonella spp.," Infect. Immun. 67: 1614-1622.

Vancott, et al. (1998) "Regulation of host immune responses by modification of Salmonella virulence genes," Nat. Med. 4: 1247-1252.

Vancott, et al. (1996) "Regulation of Mucosal and Systemic Antibody Responses by T Helper Cell Subsets, Macrophages, and Derived Cytokines Following Oral Immunization with Live Recombinant Salmonella," J. Immunol. 1504: 1514.

Vazquez-Torres, et al. (2000) "Salmonella Pathogenicity Island 2-Dependent Evasion of the Phagocyte NADPH Oxidase," Science 287: 1655-1658.

Véscovi, et al. (1996) "MG2+ as an Extracellular Signal: Environmental Regulation of Salmonella Virulence," Cell 84: 165-174.

Villarreal, et al. (1992) "Proliferative and T-cell specific interleukin (IL-2/IL-4) production responses in spleen cells from mice vaccinated with aroA live attenuated Salmonella vaccines," Microbial Pathogen. 13: 305-315.

Viret, et al. (1999) "Mucosal and Systemic Immune Responses in Humans after Primary and Booster Immunizations with Orally Administered Invasive and Noninvasive Live Attenuated Bacteria," Infect. Immun. 67: 3680-3685.

Virlogeux, et al. (1996) "Characterization of the rcsA and rcsB Genes from *Salmonella typhi*: rcsB through tviA Is Involved in Regulation of Vi Antigen Synthesis," J. Bacteriol. 178: 1691-1698.

Virlogeux, et al. (1995) "Role of the viaB locus in synthesis, transport and expression of *Salmonella typhi* Vi antigen," Microbiol. 141: 3039-3047.

Wahdan, et al. (1982) "A Controlled Field Trial of Live *Salmonella typhi* Strain Ty 21a Oral Vaccine Against Typhoid: Three-Year Results," J. Infect. Dis. 145: 292-295.

Wahdan, et al. (1980) "A controlled field trial of live oral typhoid vaccine Ty2la," Bull. World Health Org. 58: 469-474.

Wallis (2001) "Salmonella Pathogenesis and Immunity: We Need Effective Multivalent Vaccines," Vet. J. 161: 104-106.

Wallis and Galyov (2000) "Molecular basis of *Salmonella*-induced enteritis," Mol. Microbiol. 36: 997-1005.

Wang, et al. (2000) "Constitutive Expression of the Vi Polysaccharide Capsular Antigen in Attenuated *Salmonella enterica* Serovar Typhi Oral Vaccine Strain CVD 909," Infect. Immun 68: 4647-4652.

Ward, et al. (1999) "Immunogenicity of a *Salmonella typhimurium* aroA aroD Vaccine Expressing a Nontoxic Domain of Clostridium difficile Toxin A," Infect. Immun. 67: 2145-2152.

Wedemeyer, et al. (2001) "Oral Immunization With HCV-NS3-Transformed Salmonella: Induction of HCV-Specific CTL in a Transgenic Mouse Model," Gastroenterology 121: 1158-1166.

Weinstein, et al. (1998) "Differential Early Interactions between *Salmonella enterica* Serovar Typhi and Two Other Pathogenic Salmonella Serovars with Intestinal Epithelial Cells," Infect. Immun. 66: 2310-2318.

Weinstein, et al. (1997) "*Salmonella typhi* Stimulation of Human Intestinal Epithelial Cells Induces Secretion of Epithelial Cell-Derived Interleukin-6," Infect. Immun. 65: 395-404.

Weintraub, et al. (1997) "Role of αβ and γδ T Cells in the Host Response to *Salmonella* Infection as DEmonstrated in T-Cell-Receptor-Deficient Mice of Defined Ity Genotypes," Infect. Immun. 65: 2306-2312.

White, et al. (1999) "High efficiency gene replacement in *Salmonella enteritidis* chimeric fimbrins containing a T-cell epitope from Leishmania major," Vaccine 17: 2150-2161.

Wong, et al. (1974) "Vi Antigen from *Salmonella typhosa* and Immunity Against Typhoid Fever," Infect. Immun. 9: 348-353.

Woo, et al. (2001) "Unique immunogenicity of hepatitis B virus DNA vaccine presented by live attenuated *Salmonella typhimurium*," Vaccine 19: 2945-2954.

Wu, et al. (2000) "Construction and immunogenicity in mice of attenuated *Salmonella typhi* expressing Plasmodium falciparum merozoite surface protein 1 (MSP-1) fused to tetanus toxin fragment C," J. Biotechnol. 83: 125-135.

Wüthrich, et al. (1985) "Typhusepidemiologie in der Schweiz 1980-1983," Schwiez. med. Wschr. 115: 1714-1720.

Wyant, et al. (1999) "*Salmonella tyohi* Flagella Are Potent Inducers of Proinflammatory Cytokine Secretion by Human Monocytes," Infect. Immun 67: 3619-3624.

Zhang, et al. (1999) "Protection and immune responses induced by attenuated *Salmonella typhimurium* UK-1 strains," Microbial Pathogen. 26: 121-130.

Zhou, et al. (1999) "An invasion-associated *Salmonella* protein modulates the actin-bundling activity of plastin," Proc. Natl. Acad. Sci. USA 96: 10176-10181.

Curtiss, et al. (1994) "Recombinant *Salmonella* vectors in vaccine development" Dev. Biol. Stand. 82:23-33.

Galen et al. (1997) "A murine model of intranasal immunizaiton to asses the immunogenicityy of attenuated *Salmonella typhi* live vector vaccines in stimulating serium antibody responses to expressed foreign antigens," Vaccine, 15:700-708.

Hormaeche, (1979) "Genetics of natural resistance to *salmonellae* in mice," Immunology, 37:319-327.

Jones, et al. (1991) "Oral vaccination of calves against experimental salmonellosis using a double *aro* mutant of *Salmonella typhimurium*," Vaccine, 9:29-34.

Jones-Carson et al. (2007) "Systemic CD8 T cell memory response to a *Salmonella* pathogenicity island 2 effector is restricted to *Salmonella enterica* encountered in the gastrointestinal mucosa," Infect. Immun. 75:2708-2716.

Chenoweth et al. (1990) "Efficacy of ampicilin versus trimethoprim-sulfamethoxazole in a mouse model of lethal enterococcol peritonitis," Antimicrob. Agents Chemother. 34:1800-1802.

Kohler, et al. (1998) "Oral immunization with recombinant *Salmonella typhimurium* expressing a cloned porphyromonas gingivalsi hemaglutinin: effect of bookstin on mucosal systemic and immunoglobulin G subclass response," Oral Microbiol. Immunol. 13:81-88. Abstract Only.

O'Callaghan, et al. (1990) "Immunogenicity of foreign peptide epitopes expressed in bacterial envelope proteins," Res. Microbiol. 141:963-969 Abstract Only.

Schodel, et al. (1996) "Hybrid hepatitis B virus core antigen as a vaccine carrier moiety II. Expression in avirulent Salmonella spp. For mucosal immunization," Adv. Exp. Med. Biol. 397:15-21. Abstract Only.

Accession No. A51688, Genbank; "*Salmonella typhimurium*" (1997).

Accession No. A51689, Genbank; "*Salmonella typhimurium*" (1997).

Accession No. AF0208080, EMBL/Genbank; Aug. 7, 1998 Valdivia et al., *Salmonella typhimurium* pathogenicity island 2.

Accession No. AJ224892, Genbank; "*Salmonella typhimurium* ssaE, sseA, sseB, sscA, sseC, sseD, sseE, sscB, sseF, sseG, ssaG, ssaH, ssaI genes and partial ssaD, ssaJ genes," (1998).

Accession No. AJ224978, Genbank; "*Salmonella typhimurium*," (1999).

Accession No. J05534, EMBL, "*Escherichia coli* ATP-dependent clp protease proteolytic component (clpP) gene, complete cds," (Jun. 28, 1990). cited by other.

Accession No. 029579, Plunkett, EMBL ID No. EC29479, (Mar. 4, 2000).

Accession No. U51867 (Mar. 4, 2000), Stein, EMBL ID No. ST51867.

Accession No. U51927, Genbank; "*Salmonella typhimurium* SpiR and SpiB genes, partial cds, and SpiC and SpiA genes, complete cds," (1996).

Accession No. X56793, EMBL, "*S. enterica* (group B) rfb gene cluster," (May 22, 1991). cited by other.

Accession No. X61917, EMBL, "*S. enterica* rlbJ gene cluster," (Jun. 19, 1992). cited by other.

Accession No. X99944, Genbank; "*S. typhimurium* ssaA, ssaR, ssaT and ssaU genes," (1997).

Accession No. Y09357, Genbank; "*S. typhimurium* ssaJ, ssaK, ssaL, ssaM, ssaV, ssaN, ssaO, ssaP, ssaQ genes," (1997).

Accession No. Z23278, EMBL/Genbank, "*E. coli* ClpX gene, complete cds," (Jul. 13, 1993). cited by other.

Accession No. Z95891, EMBL/Genbank; Jan. 8, 1998 *Salmonella typhimurium* ssrA and ssrB genes.

Adachi, et al. (1994) "Isolation of Dictyostelium discoideum cytokinesis mutants by restriction enzyme-mediated integration of the blasticidin S resistance marker," Biochem. Biophys. Res. Comm. 205, 1808-1814 (1994).

Albus et al. (1991) "Virulence of *Staphylococcus aureus* mutants altered in type 5 capsule production," Infect. Immun. 59, 1008-1014.

Aldous, (1994) "Fast Track to Disease Genes", Science 265:2008-2010.

Anthony et al. (1991) "Transformation and allelic replacement in Francisella spp," J. Gen. Microbiol. 137, 2697-2703.

Artiguenave et al. (1997) "High-efficiency transposon mutagenesis by electroporation of a *Pseudomonas fluorescens* strain," FEMS Microbiol. Lett. 153, 363-369.

Bergman et al., (1994) "The lcrB (yscN/U) gene cluster of *Yersinia pseudotuberculosis* is involved in Yop secretion and shows high homology to the spa gene clusters of *Shigella flexneri* and *Salmonella typhimurium*," J. Bacteriol. I 76(9):2619-2626.

Blasco, et al., (1990) "Nitrate reductases of *Escherichia coil*: Sequence of the second nitrate reductase and comparison with that encoded by the narGHJI operon," Mol. Gen. Genet. 222:104-111.

Bolker et al. (1995) "Tagging pathogenicity genes in Ustilago maydis by restriction enzyme-mediated integration (REMI)," Mol. Gen. Genet. 248, 547-552.

Brown et al. (1997) 19th Fungal Genetics Conference, Mar. 18-23, 1997, Asilomar Conference Centre, Pacific Grove, CA.

Brown, et al., "Molecular analysis of he rfb gene cluster of Salmonella serovar muenchen (strain M67): the genetic basis of the polymorphism between groups C2 and B," Molecular Microbiology 6(10): 1385-1394 (1992).

Buchmeir et al., "Recombinant-deficient mutants of Salmonella typhimurium are avirulent and sensitive to the oxidative burst of macrophages," Mol. Microbiol. 7(6):933-936 (1993).

Burgess et al., (1990) "Possible dissociation of the heparin-binding and mitogenic activities of heparin-binding (acidic fibroblast) growth factor-1 from its receptor-binding activities by site-directed mutagenesis of a single lysine residue," J. Cell. Biol. 111:2129-2138.

Camilli et al. (1990) "Insertional mutagenesis of Listeria monocytogenes with a novel Tn917 derivative that allows direct cloning of DNA flanking transposon insertions," J. Bacteriol. 172, 3738-3744.

Carter & Collins, (1974) "The Route of Enteric Infection In Normal Mice", J. Exp. Med., 139:1189-1203.

Cheung et al. (1992) "Regulation of exoprotein expression in Staphylococcus aureus by a locus (sar) distinct from agr," Proc. Natl. Acad. Sci. USA 89, 6462-6466.

Chiang & Mekalonas (1998) "Use of signature-tagged transposon mutagenesis to identify Vibrio cholerae genes critical for colonization," Mol. Microbiol. 27, 797-805.

Chuang et al., (1993) "Global regulation of gene expression in Eschericia coli," J. of Bacteriology 175: 2026-2036.

Cirillo, et al., "Macrophage-dependent induction of the Salmonella pathogenicity island 2 type III secretion system and its role in intracellular survival," Mol. Microbiol. 30: 175-188 (1998).

Coghlan, "Bar codes to tag bad genes,"0 New Scientist p. 18 (Jul. 29, 1995).

Correia et al. (1995) "Insertional inactivation of binding determinants of Streptococcus crista CC5A using Tn916," Oral Microbiol. lmmunol. 10, 220-226. Abstract Only.

Dei Wick et al., (1998) "Mutations in Salmonella Pathogenicity Island 2 (SPI2) Genes Affecting Transcription of SPI1 Genes and Resistance to Antimicrobial Agents, "J. Bacteriol. 180(18):4775-4780.

Dolganov & Grossman (1993) "Insertional inactivation of genes to isolate mutants of Synechococcus sp. strain PCC 7942:isolation of filamentous strains," J. Bacteriol. 175, 7644-7651.

Dunyakl, et al., "Identification of Salmonella pathogenecity island 2 (SPI2) genes in Salmonella cholaraesuis using signature-tagged mutagenesis," Abstracts of the 97.sup.th General Meeting of the American Society for Microbiology B-275, May 4-8, 1997.

Fields, et al., (1989) "A Salmonella Locus That Controls Resistance Tto Microbicidal Proteins From Phagocytic Cells", Science, 243:1059-1062.

Finlay, et al., (1988) "Identification Aand Characterization Of TnphoA Mutants Of Salmonella That Are Unable to Pass Through A Polarized MDCK Epithelial Cell Monolayer", Mol. Microbiol., 2:757-766.

Fitts, (1985) "Development of a DN-DNA hybridization test for the presence of salmonella in foods," Food Technology 95-102 (1985).

Freestone, et al., (1977) "Stabilized 17D strain yellow fever vaccine: dose response studies, clinical reactions and effects on hepatic function," Journal of Biological Standardization 5:181-186.

Gaillard et al. (1986) "Transposon mutagenesis as a tool to study the role of hemolysin in the virulence of Listeria monocytogenes," Infect. Immun. 52, 50-55.

Galan and Curtiss, "Cloning and molecular characterization of genes whose products allow Salmonella typhimurium to penetrate tissue culture cells," Proc. Natl. Acad. Sci. USA 86(16):6383-6387 (1989).

Galan and Curtiss, "Virulence and vaccine potential of phoP mutants of Salmonella typhimurium," Microb. Pathog. 6(6):433-443 (1989).

Galan, et al., (1992) "Molecular And Functional Characterization Of The Salmonella Invasion Gene invA: Homology Of InvA To Memebers Of A New Protein Family." J. Bacteriol. 174:4338-4349.

Gentschev, et al., (1996) "Development of antigen-delivery systems, based on the Escherichia coli hemolysin secretion pathway," Gene 179: 133-140 (1996). Abstract Only.

Gentschev, et al., (1994) "Synthesis and secretion of bacterial antigens by attenuated Salmonella via the Escherichia coli hemolysin secretion system," Behring Inst. Mitl. 95: 57-66.

Groisman & Ochman, (1994) "How to Become a Pathogen", Trends Microbiol., 2:289-293.

Groisman & Saie, "Salmonella Virulence: New Clues To Intramacrophage Survival", Trends in Biochem. Sci., 15:30-33 (1990).

Groisman and Ochman, "Cognate gene clusters govern invasion of host epithelial cells by Salmonella typhimurium and Shigella flexneri," EMBO J. I2(10):3779-3787 (1993).

Groisman, et al., (1993) "Molecular, Functional And Evolutionary Analysis of Sequences Specific To Salmonella", Proc. Natl. Acad. Sci. USA, 90:1033-1037.

Groisman, et al., (1989) "Salmonella Typhimurium phoP Virulence Gene Is A Transcriptional Regulator", Proc. Natl. Acad. Sci. USA, 86:7077-7081.

Guzman, et al., "Antibody Responses in the Lungs of Mice following Oral Immunization with Salmonella typhimurium aroA and Invasive Escherichia coli Strains Expressing the Filamentous Hemagglutinin of Bordetella pertussis," Inf. Immun. 59:4391-4397 (1991).

Guzman, et al., (1991) "Direct Expression of Bordetella pertussis Filamentous Hemagglutinin in Escherichia coli and Salmonella typhimurium arpA." Inf.Immun. 39:3787-3795.

Guzman, et al., (1992) "Expression of Bordetella pertussis filamentous hemagglutinin in Escherichia coli using a two cistron system," Microbiol. Pathogenics 12:383-389.

Guzman et al., (1993) "Use of Salmonella spp carrier strains to delivery Bordetella pertussis antigens in mice using the oral route," in Biology of Salmonella (Cabello, et al., eds.) Plenum Press: New York, NY.

Han et al. (1997) "Tn5 tagging of the phenol-degrading gene on the chromosome of Pseudomonas putida," Mol. Cells 7, 40-44.

Hensel, "Salmonella Pathogenicity Island 2," Mol. Microbiol. 36:1015-1023 (2000).

Hensel, et al., (1997) "Analysis of the boundaries of Salmonella pathogenicity island 2 and the corresponding chromosomal region of Escherichia coli K-12," Journal of Bacteriology 179:1105-1111.

Hensel et al., (1997) "Functional analysis of ssaJ and ssaK/U operon, 13 genes encoding components of the type III secretion apparatus of Salmonella pathogenicity island 2," Mol. Microbiol. 24(1): 155-167.

Hensel, et al., (1998) "Genes encoding putative effector proteins of the type III secretion system of Salmonella pathogenicity island 2 are required for bacterial virulence and proliferation in macrophages," Mol. Microbiol. 30:163-174.

Hensel, et al., (1999) "Molecular and functional analysis indicates a mosaic structure of Salmonella pathogenicity island 2," Mol. Microbiol. 31:489-496.

Hensel, et al., (1995) "Simultaneous Identification of Bacterial Virulence Genes by Negative Selection", Science, 269:400-403.

Hensel, et al., (1999) "The genetic basis of tetrathionate respiration in Salmonalla typhimurium," Mol. Microbiol. 32:275-287.

Holdon "The type III secretion system of Salmonella Pathogenicity Island 2," FEBS Advanced Course—Protein Export and Assembly in Bacteria, Lunteren, The Netherlands; Apr. 25-May 1, 1998.

Holland, et al., "Tn916 Insertion Mutagenesis in Escherichia coli and Haemophilus Influenzae Type b Following Conjugative Transfer", J. Gen. Microbiol., 138:509-515 (1992).

Juntenen-Backman, et al., (1987) "Safe immunization of allergic children against measles, mumps, and rubella," AJDC 141:1103-1105.

Kahrs et al. (1994) "Generalized transposon shuttle mutagenesis in Neisseria gonorrhoeae: a method for isolating epithelial cell invasion-defective mutants," Mol. Microbiol. 12, 819-831. (Abstract only).

Kim et al. (1997) "The hrpA and hrpC operons of Erwinia amylovora encode components of a type III pathway that secretes harpin," J. Bacteriol. 179(5), 1690-1697.

Lee & Falkow, (1994) "Isolation of Hyperinvasive Mutants of Salmonella", Methods Enzymol., 265:531-545.

Lee, (1997) "Type III secretion systems: machines to deliver bacterial proteins into eukaryotic cells!" Trends Microbiol. 5(4): 148-156.
Levine, et al., "Salmonella vaccines" in New Antibacterial Strategies (Neu, HC, ed.), pp. 89-104, (Churchill Livingstone:London, 1990).
Levine, et al., eds., (1997) "Attenuated Salmonella as a live vector for expression of foreign antigens," in New Generation Vaccines, 2nd ed., Marcell Dekker: New York, Chapter 27, pp. 331-361.
Listitsyn, et al., (1993) "Cloning the Difference Between Two -Complex Genomes", Science, 259:946-951.
Lististyn, et al., (1994) "Direct Isolation Of Polymorphic Markers Linked To A Trait By Genetically Directed Representational Difference Analysis", Nature Genetics, 6:57-63.
Lu, et al., (1994) "Tagged Mutations At the Tox1 Locus of Cochliobolus Heterostrophus by Restriction Enzyme-Mediated Integration", Proc. Natl. Acad. Sci. USA, 91:12649-12653.
Mahan, et al., (1993) "Selection Of Bacterial Virulence Genes That Are Specifically Induced In Host Tissues", Science, 259:686-688.
Maurizi et al., (1990) "Sequence and Structure of Clp P, the Proteolytic Component of the ATP-Dependent Clp Protease of *Escherichia coli*," J. Biol. Chem., 265(21):12536-45.
Mecsas & Strauss, "Molecular mechanisms of bacterial virulence: type III secretion and pathogenicity islands," Emerging Infectious Diseases 2(4): 271-288 (1996).
Medina et al., "Pathogenicity island 2 mutants of *S. typhimurium* are efficient carriers for heterologous . . . ", Infection and Immunity, vol. 67, No. 3, Mar. 1999, pp. 1093-1099.
Mei et al. (1997) "Identification of *Staphylococcus aureus* virulence genes in a murine model of bacteraemia using signature-tagged mutagenesis," Mol. Microbiol. 26, 399-407.
Mejia-Ruiz et al. (1997) "Isolation and characterization of an Azotobacter vinelandii algK mutant.," FEMS Microbiol. Lett. 156, 101-106.
Miller, et al., (1989) "A Two-Component Regulatory System (phoP-phoQ) Controls *Salmonella Typhimurium* Virulence", Proc. Natl. Acad. Sci. USA, 86:5054-5058.
Miller, et al., (1989) "Isolation of Orally Attenuated *Salmonella Typhimurium* Following TnphoA Mutagenesis", Infection Immun., 57:2758-2763.
Morrison et al. (1984) "Isolation of transformation-deficient *Steptococcus pneumoniae* mutants defective in control of competence, using insertion-duplication mutagenesis with the erythromycin resistance determinant of pAM beta 1," J. Bacteriol. 159, 870-876.
Myers & Myers (1997) "Isolation and characterization of a transposon mutant of *Shewanella putrefaciens* Mr-1 deficient in fumarate reductase," Lett. Appl. Microbiol. 25, 162-168.
Nelson, et al., (1993) "Genomic Mismatch Scanning: A New Approach To Genetic Linkage Mapping", Nature Genetics, 4:11-17.
Norgan et al. (1989) "A method for allelic replacement that uses the conjugative transposon Tn916: deletion of the emm6. 1 allele in *Steptococcus pyogenes* JRS4," Infect. Immun. 57, 3846-3850.
Ochman & Groisman, "Distribution of pathogenicity islands in Salmonella sp." Infection and Immunity 64:5410-12 (1996).
Ochman et al., "Identification of a pathogenicity island required for Salmonella . . ", The National Academy of Sciences of USA, vol. 93, Jul. 1996, pp. 7800-7804.
Pang et al. (1998) "Typhoid fever—important issues still remain," Trends Microbiol. 6, 131-133.
Pascopella, et al., "Use Of In Vivo Complementation In *Mycobacterium Tuberculosis* To Identify A Genomic Fragment Associated With Virulence", Infection Immun., 62:1313-1319 (1994).
Pelicic et al. (1998) "Genetic advances for studying *Mycobacterium tuberculosis* pathogenicity," Molecular Microbiology 28, 413-420.
Piatti, et al., "Cloning and Characterization of *S. typhi*," Sociela Italiana di Microbiologia Medica Odontoiatrica e Clinica '93 (Translation), p. 82, 1993.
Polissi et al. (1997) Fourth European Meeting on the Molecular Biology of the Pneumococcus, Abstract A.18.
Ramakrishnan et al. (1997) "*Mycobacterium marinum* causes both long-term subclinical infection and acute disease in the leopard frog (Rana pipiens)," Infect. Immun. 65, 767-773.

Regue et al. (1991) "A generalized transducing bacteriophage for Serratia marcescens," Res. Microbiol. 142, 23-27.
Rella et al. (1985) "Transposon insertion mutagenesis of *Pseudomonas aeruginosa* with a Tn5 derivative: application to physical mapping of the arc gene cluster," Gene 33, 293-303.
Roberts et al. (1988) "Cloning of the egl gene of *Pseudomonas solanacearum* and analysis of its role in phytopathogenicity," J. Bacteriol. 170, 1445-1451.
Roos et al. (1997) "Tagging genes and trapping promoters in Toxoplasma gondii by insertional mutagenesis,"Methods 13, 112-122.
Rott et al. (1996) "At least two separate gene clusters are involved in albicidin production by *Xanthomonas albilineans*," J. Bacteriol. 178, 4590-4596.
Roudier et al. (1992) "Characterization of translation termination mutations in the spy operon of the Salmonella virulence plasmid pSDL2," J. Bacteriology 174, 6418-6423.
Russman, et al., (1998) "Delivery of epitopes by the *Salmonella* type III secretion system for vaccine development," Science 281:585-568.
Schiestl & Petes (1991) "Integration of DNA fragments by illegitimate recombination in Saccharomyces cerevisiae," Proc. Natl. Acad. Sci. USA 88, 7585-7589.
Sharetzsky et al. (1991) "A novel approach to insertional mutagenesis of *Haemophilus influenzae*," J. Bacteriol. 173, 1561-1564.
Shea, et al., (1996) "Identification of a virulence locus encoding a second type III secretion system in *Salmonella typhimurium*," Proc. Natl. Sci. USA 93:2593-2597.
Shea, et al., (1999) "Influence of the *Salmonella typhimurium* pathogenicity island 2 type III secretion system on bacterial growth in the mouse," Infection and Immunity 67:213-219.
Slauch, et al., (1994) "In Vivo Expression Technology For Selection Of Bacterial Genes Specifically Induced In Host Tissues", Methods Enzymol, 235:481-492.
Smtih, et al., (1995) "Genetic Footprinting: A Genomic Strategy For Determining A Gene's Function Given Its Sequence", Proc. Natl. Acad. Sci. USA, 92:6479-6483.
Smith, et al., (1994) "Virulence Of *Aspergillus Fumigatus* Double Mutants Lacking Restriction And An Alkaline Protease In A Low-Dose Model Of Invasive Pulmonary Aspergillosis", Infection Immun., 62(4):1313-1319.
Staendner, et al., "Identification of *Salmonella typhi* promoters activated by invasion of eukaryotic cells," Mol. Microbiol. 18:891-902 (1995).
Stojilijovik, et al., (1995) "Ethanolamine utilization in *Salmonella typhurium*: nucleotide sequence, protein expression, and mutational analysis of the cchA cchB eutE eutJ eutH gene cluster", J. Bacteriol., 177(5)1357-66.
Subramanian et al. (1992) "Rapid mapping of *Escherichia coli*::Tn5 insertion mutations by REP-Tn5 PCR" PCR Methods 1, 187-192.
Sutherland & Springett, (1987) "Effectiveness of BCG vaccination in England and Wales in 1983," Tubercle 68(2):81-92 (1987).
Tam & Lefebvre (1993) "Cloning of flagellar genes in *Chlamydomonas reinhardtii* by DNA Insertional mutagenesis" Genetics 135, 375-384. (Abstract only).
Trieu-Cuot et al. (1991) "An integrative vector exploiting the transposition properties of Tn1545 for insertional mutagenesis and cloning of genes from gram-positive bacteria," Gene 106, 21-27.
Tsolis et al., (1995) "Role of *Salmonella typhimurium* Mn-superoxide dismutase (SodA) in protection against early killing by J774 macrophages," Infect. Immun. 63(5):1739-1744.
Tzschaschel, et al., (1996) "An *Escherichia coli* hemolysin transport system-based vector for the export of polypeptides: export of Shiga-like toxin IleB subunit by *Salmonella tyhphimurium* aroA," Nature Biotechnol. 14: 765-769.
Valentine, et al., (1998) "Identification of Three Highly Attenuated *Salmonella typhimurium* Mutants That are Moe Immunogenic and Protective in Mice than a Prototypical aroA Mutant," Infect. Immun. 66:3378-3383.
Walker, et al., (1992) "Specific Lung Mucosal and Systemic Immune Responses after Oral Immunization of Mice with *Salmonella typhimurium* aroA, *Salmonella typhi* Ty21a, and invasive *Escherichia coli* expressing Recombinant Pertussis Toxin S1 Subunit," Inf. Immun. 60:4260-4268.

Walsh & Cepko, (1992) "Wildespread Dispertion of Neuronal Clones Across Functional Regions of the Cerebral Cortex", Science, 255:434-440.

Wooley et al. (1989) "Transfer of Tn1545 and Tn916 to *Clostridium acetobutylicum*," Plasmid 22, 169-174.

Bainton et al., (1979) "Immunity of children to diphtheria, tetanus, and poliomyelitis," British Medical Journal 1:854-57.

Jiang et al. (1991) Structure and sequence of the rfb (O antigen) gene cluster of *Salmonella serovar* typhimurium (strain LT2). Mol. Microbiol. 5:695-713.

Leahy et al. (1993) "Transposon mutagenesis in Acinetobacter calcoaceticus RAG-I," J. Bacteriol. 175, 1838-1840.

Lazar et al., (1988) "Transforming growth factor alpha: mutation of aspartic acid 47 and leucine 48 results in different biological activities, "Mol. Cell. Biol. 8:1247-1252.

Valdivia & Falkow, (1997) "Fluorescence-based isolation of bacterial genes expressed within host cells," Science 277: 2007-2011.

* cited by examiner

ATTENUATED MICROORGANISMS FOR THE TREATMENT OF INFECTION

CROSS-REFERENCE TO RELATED APPLICATION

This application is a continuation of U.S. application Ser. No. 10/822,053, filed Apr. 8, 2004, now U.S. Pat. No. 7,211,264, which is a continuation of Ser. No. 09/569,601, filed May 9, 2000, now U.S. Pat. No. 6,756,042, the disclosure of each of which is incorporated herein by reference in their entireties, including any figures, tables, nucleic acid sequences, amino acid sequences, and drawings.

FIELD OF THE INVENTION

This invention relates to attenuated microorganisms that can be used in vaccine compositions for the prevention or treatment of bacterial or viral infections.

BACKGROUND TO THE INVENTION

It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed preparations, live vaccines are able to induce potent cell-mediated responses which may be connected with their ability to replicate in antigen-presenting cells, such as macrophages.

There has been a long history of the use of live attenuated *Salmonella* vaccines as safe and effective vaccines for the prevention of salmonellosis in animals and humans. Indeed, the live attenuated oral typhoid vaccine, Ty21a (Vivotif), manufactured by the Swiss Serum Vaccine Institute, has proved to be a very successful vaccine for the prevention of typhoid fever and has been licensed in many countries including the US and Europe.

However, the attenuation of this strain was achieved using chemical mutagenesis techniques and the basis of attenuation of the strain is not fully understood. Because of this, the vaccine is not ideal in terms of the number of doses (currently four) and the number of live organisms that have to be given at each dose.

Modern molecular biology techniques, coupled with the increasing knowledge of *Salmonella* pathogenesis, has led to the identification of several genes that are essential for the in vivo growth and survival of the organisms. This has provided new gene targets for attenuation, leading to the concept that future vaccine strains can be 'rationally' attenuated by introducing defined non-reverting mutations into selected genes known to be involved in virulence. This will facilitate the development of improved vaccines, particularly in terms of the immunogenicity and therefore the number of doses that have to be given.

Although many attenuated strains of *Salmonella* are now known, few have qualified as potential vaccine candidates for use in humans. This may be due in part to the need to balance the immunogenicity of the vaccine with the possibility of the *Salmonella* microorganism becoming reactive.

It is clear that the selection of appropriate targets for attenuation which will result in a suitable vaccine candidate, is not straightforward and cannot easily be predicted. Many factors may influence the suitability of the attenuated strain as an appropriate vaccine, and there is much research being carried out to identify suitable strains. For example, many attenuated strains tested as vaccine candidates lead to vaccinemia or abscesses in the patient.

It is therefore desirable to develop a vaccine having a high degree of immunogenicity with reduced possibility of the microorganism strain reverting to an reactive form and which exhibits a good safety profile with limited side effects.

SUMMARY OF THE INVENTION

The present invention is based on the finding that two specific attenuating mutations introduced into a *Salmonella* microorganism can produce a vaccine having a high degree of immunogenicity and a low risk of the microorganism reverting to a reactive form. The resulting vaccine strains exhibit a good side-effect profile.

The first mutation is contained within a region of the *Salmonella* pathogenicity island two (Spi2); the second is an auxotrophic mutation, i.e. a mutation to disrupt the expression of a gene that encodes a protein required in a biosynthetic pathway.

According to a first aspect of the invention, a *Salmonella* microorganism has an attenuating mutation which disrupts the expression of a gene located within the Spi2 pathogenicity island, and an independent auxotrophic mutation. The preferred attenuating mutation is within the apparatus gene ssaV, and the preferred auxotrophic mutation is within aroC.

The microorganism preferably further comprises one or more heterologous antigens or therapeutic proteins, for example antigens for pathogenic *E. coli, Shigella*, hepatitis A, B or C, Herpes Simplex Virus and Human papilloma virus. Therefore, the microorganism may act as a delivery vehicle to immunise against infections other than *Salmonella*.

The *Salmonella* microorganisms may be used to manufacture a vaccine composition which may be administered to a patient via the intravenous or oral route, in a method for the treatment of a bacterial or viral infection, e.g. for the treatment of typhoid.

The attenuated *Salmonella* microorganisms of the present invention form vaccines which surprisingly stimulate mucosal as well as systemic immunity. Further, the microorganisms do not cause spleen abscesses in an animal model, whereas mutants with single mutations do. This is a particular advantage of the double mutants as defined herein.

DESCRIPTION OF THE INVENTION

The microorganisms and vaccine compositions of the present invention may be prepared by known techniques.

The choice of particular *Salmonella* microorganism and the selection of the appropriate mutation, can be made by the skilled person without undue experimentation. A preferred microorganism is *Salmonella typhimurium*.

A first mutation may be introduced into a gene located within the region of the *Salmonella* pathogenicity island 2, this region being disclosed in WO-A-9617951.

The *Salmonella* pathogenicity island two (Spi2) is one of two classical pathogenicity islands located on the *Salmonella* chromosome. Spi2 comprises several genes that encode a type III secretion system involved in transporting Spi2 encoded virulence-associated proteins (so-called effector proteins) outside of the *Salmonella* bacteria and potentially directly into target host cells such as macrophages. Part of Spi2 (the apparatus genes) encodes the secretion apparatus of the type III system. Spi2 is absolutely essential for the pathogenesis and virulence of *Salmonella* in the mouse, an observation now documented by several different groups around the world. *S. typhimurium* Spi2 mutants are highly attenuated in mice challenged by the oral, intravenous and intraperitoneal routes of administration.

The Spi2 gene may be either an apparatus gene or an effector gene. Preferably, the gene is an apparatus gene. The apparatus genes located within Spi2 are now well characterised; see for example Hensel et al., Molecular Microbiology (1997); 24(1): 155-167. Genes suitable for use in the present invention include ssaV, ssaJ, ssaK, ssaL, ssaM, ssaO, ssaP, ssaQ, ssaR, ssaS, ssaT, ssaU and ssaH genes.

The mutation in the Spi2 region does not necessarily have to be within a gene to disrupt the function. For example, a mutation in an upstream regulatory region may also disrupt gene expression, leading to attenuation. Mutations in an intergenic region may also be sufficient to disrupt gene function.

In a preferred embodiment of the invention, the apparatus gene is ssaV. In a separate preferred embodiment, the mutation lies within an intergenic region between ssaJ and ssaK.

The second mutation is termed an "auxotrophic mutation" as it disrupts a gene which is essential in a biosynthetic pathway. The biosynthetic pathway is one present in *Salmonella*, but not present in mammals. Therefore, the mutants cannot depend on metabolites found in the treated patient to circumvent the effect of the mutation.

Suitable genes for the auxotrophic mutation, include any aro gene, e.g. aroA, aroC, aroD and aroE.

In a preferred embodiment of the invention, the vaccine composition comprises a *Salmonella* microorganism having attenuating mutations in ssaV and aroC.

The mutations may be introduced into the microorganism using any known technique. Preferably, the mutation is a deletion mutation, where disruption of the gene is caused by the excision of nucleic acids. Alternatively, mutations may be introduced by the insertion of nucleic acids or by point mutations. Methods for introducing the mutations into the specific regions will be apparent to the skilled person.

In addition to the two mutations, the *Salmonella* microorganism may also comprise heterologous antigens. The attenuated microorganism can therefore act as a delivery vehicle for administering antigens against other bacterial or viral infections. Antigens which are suitable for use in this way will be apparent to the skilled person and include:

Pathogenic *E. coli* antigens, i.e. ETEC
Hepatitis A, B and C antigens
Lime disease antigens
*vibrio cholera* antigens
*Helicobacter* antigens
Herpes Simplex virus antigens
Human papilloma virus antigens This system also has the potential to deliver therapeutic proteins, e.g. cytokines, for the treatment of patients, e.g. patients infected with hepatitis. Methods for the delivery of heterologous antigens or therapeutic proteins using the vaccine compositions will be apparent to the skilled person.

Vaccines made using the microorganisms of the invention have application to the treatment of infections in human patients and in the treatment of veterinary infections.

The double mutation provides an effective means to attenuate the microorganism to provide a safe vaccine candidate.

The vaccine compositions provide effective protection even in immunocompromised patients, and importantly offer a low risk in developing spleen abscesses. Spleen abscesses have been identified using vaccines based on a single mutation, and therefore the present compositions may offer a substantial benefit to patients.

To formulate the vaccine compositions, the mutant microorganisms may be present in a composition together with any suitable pharmaceutically acceptable adjuvant, diluent or excipient. Suitable formulations will be apparent to the skilled person. The formulations may be developed for any suitable means of administration. Preferred administration is via the oral or intravenous routes and the vaccines are live attenuated *Salmonella* microorganisms. The number of microorganisms that are required to be present in the formulations can be determined and optimised by the skilled person. However, in general, a patient may be administered approximately $10^7$-$10^{10}$ CFUs, preferably approximately $10^8$-$10^9$ CFUs in a single dosage unit.

The following Examples illustrate the invention.

Example 1

This Example describes the preparation of a mutant strain designated ZH9 which has activity as a human oral typhoid vaccine. The strain is derived from the virulent *S. typhi* strain Ty2, originally isolated from a case of typhoid. The derived strain has a defined mutation within purA and aroA.

Ty2 for the Construction of ZH9

*S. typhi* Ty2 was originally isolated from an individual with typhoid fever in 1916 and has been used for the derivation of all licensed typhoid vaccines. The strain was obtained from the PHLS national culture collection at Colindale. It was obtained as a lyophilised culture, the NCTC number being 8385.

Cloning the *S. typhi* aroC Gene from *S. typhi* Ty2

*S. typhi* Ty2 was recovered from stock and grown overnight in Luria Bertani (LB) broth. The cells were harvested and whole cell DNA was prepared. DNA fragments of *S. typhi* Ty2 DNA were generated by partial cleavage with the restriction enzyme Sau3A and the resulting fragments were ligated to BamH1 cleaved pHC79 to generate a cosmid library of *S. typhi* Ty2 DNA using *E. coli* HU835 as recipient. To isolate the DNA encoding aroC from the *S. typhi* DNA, the cosmid library was used to transduce *E. coli* AB2849 which harbours a mutation in the aroC gene and is dependant on aromatic compounds for growth. The transduction mixture was plated onto minimal medium lacking aromatic compounds and incubated at 37° C. A number of isolated colonies were observed following overnight incubation. These bacteria had presumably arisen as a consequence of complementation of the aroC mutation in AB2849 by a cosmid clone harbouring the intact aroC gene from. Cosmid DNA from one of these strains was purified. A 5.2 kb HindIII fragment from this cosmid was cloned into pUC18 to give plasmid pTAC2 which was able to complement the deletion of aroC in AB2849, demonstrating that it contains the *S. typhi* aroC gene.

Generation of a Defined Deletion of the Cloned *S. typhi* Ty2 aroC

A defined 600 bp deletion was created within the cloned aroC gene using PCR. The oligonucleotide primers used in the PCR were designed using the published DNA sequence of the *S. typhi* aroC gene (Acc. M27715). The DNA 5' to the aroC gene was amplified from pTAC2 using primers SEQ ID NO. 3 and SEQ ID NO. 1. SEQ ID NO. 3 anneals to vector DNA, SEQ ID NO. 1 anneals to the 5' region of aroC. The DNA 3' to the aroC gene was amplified using primers SEQ ID NO. 4 and SEQ ID NO. 2. SEQ ID NO. 4 anneals to vector DNA, SEQ ID NO. 2 anneals to the 3' region of aroC. The resulting PCR products had XbaI sites incorporated into the 5' ends to facilitate cloning. The fragments were cloned into the vector pUC18. The final plasmid construct designated pMIAC23 contains a defined deletion of aroC (position 544 to 1143) on a 4.8 kb HindIII fragment. The HindIII fragment is inserted at the HindIII site of pUC18. A single XbaI site is present at the site of the aroC deletion.

Introduction of the aroC Mutation into the *S. typhi* Ty2 Genome

The suicide plasmid pCVD442 (Donnenberg & Kaper, Infection and Immunity, 1991; 59: 4310-4317) was used as a vector to introduce the aroC deletion into the genome of *S. typhi* Ty2. The 4.8 kb HindIII fragment containing the aroC deletion was isolated from pMIAC23 and the ends made blunt by using the Stratagene DNA polishing kit. Plasmid pCVD442 was linearized by digestion with SmaI, treated with alkaline phosphatase and ligated to the blunt-ended fragments. The required construct was isolated and denoted pYCVC21.

pYCVC21 was introduced into *S. typhi* Ty2 by using a standard electroporation protocol. The plasmid was able to integrate into the Ty2 genome following recombination between the homologous regions on the plasmid and the genome to give ampicillin resistant transformants. These transformants contained a copy of both the original wild type aroC and the deleted aroC gene. Growing these strains in the absence of ampicillin allowed for a second recombination event to occur which resulted in loss of the pCVD442 DNA sequences and one copy of the aroC gene, either the wild-type copy or the deleted copy. *S. typhi* Ty2 bacteria which had undergone this second recombination event were identified as ampicillin sensitive derivatives which were able to grow in the presence of 5% sucrose (pCVD442 carries the sacB gene which when expressed results in a sucrose sensitive phenotype). Strains that had retained only the deleted aroC gene were initially identified as strains that were unable to grow on minimal media plates in the absence of a supplement of aromatic compounds. The aroC genotype was confirmed by using PCR analysis. Primers having SEQ ID NO. 5 and SEQ ID NO. 6 gave a product of 994 bp for the wild type aroC and 400 bp for the deleted aroC gene. Sequence analysis of the resulting PCR products confirmed the presence of the required deletion in 5 individual isolates designated DTY6, DTY7, DTY8, DTY9 and DTY10. These strains were stored in Microbank vials at −70° C. for long term storage. Strain DTY8 was chosen for further manipulation.

Introduction of an ssaV Mutation into the *S. typhi* aroC Mutant DTY8

A 7.5 kb PstI fragment containing the ssaV region of *S. typhi* was amplified from a total DNA preparation by using PCR and cloned into the vector pCR2.1 (Invitrogen). The PCR oligonucleotide primers employed, having SEQ ID NO. 7 and SEQ ID NO. 8, were designed to the *S. typhimurium* SPI2 sequence. The resulting plasmid construct was designated pTYSV21.

A plasmid construct possessing a deletion of the ssaV gene was derived from pTYSV21 by using reverse orientation PCR. Primers annealing to the 5' (SEQ ID NO. 9) and 3' (SEQ ID NO. 10) regions of the ssa V open reading frame were designed to the *S. typhimurium* Spi2 sequence. An AvrII restriction site was incorporated into the 5' region of each primer, an XbaI site was incorporated into SEQ ID NO. 10. The XbaI site serves as a tag for the ssaV mutation so it can be detected easily by restriction analysis. The resulting PCR product was subjected to digestion with AvrII and the backbone plasmid molecules purified following agarose gel electrophoresis. Re-circularisation of the resulting fragments at the AvrII sticky-ends gave the required deletion construct pYDSV1. pYDSV1 contains a 5.5 kb PstI fragment with a defined 1894 bp deletion within the ssa V open reading frame.

The suicide plasmid pCVD442 was used as a vector to introduce the ssaV deletion into the genome of the *S. typhi* Ty2 aroC mutant DTY8. The 5.5 kb PstI fragment containing the ssa V deletion was isolated from pYDSV1 and the ends made blunt by treatment with Kienow DNA polymerase. Plasmid pCVD442 was linearized by digestion with SmaI, treated with alkaline phosphatase and ligated to the blunt-ended fragments. The required construct was isolated and denoted pYDSV214.

pYDSV214 was introduced into *S. typhi* DTY8 by using electroporation. Ampicillin-resistant transformants were selected and then grown in the absence of amplicillin to allow for loss of the pCVD442 DNA sequences and one copy of the ssa V gene, either the wild-type copy or the deleted copy. Strains that had undergone this second recombination event were identified as ampicillin-sensitive, sucrose-resistant colonies. Strains that had retained only the deleted ssa V gene were identified by using PCR analysis. Primers having SEQ ID NO. 11 and SEQ ID NO. 12 gave a product of 2485 bp for the wild type ssaV and 591 bp for the deleted ssaV gene. Sequence analysis of the resulting PCR products confirmed the presence of the required deletion in 5 individual isolates, ZH2, ZH4, ZH6, ZH7 and ZH9. STrain ZH9 was chosen for manufacture of a CGMP master cell bank.

Example 2

This Example describes the preparation of a *S. typhimurium* mutant strain designated WT05 which has vaccine activity against human gastroenteritis. The strain is derived from the known human virulent *S. typhimurium* strain TML.

TML for the Construction of WT05

TML was originally isolated from a patient suffering from gastroenteritis and was identified in the laboratories of Dr John Stevens at Birmingham University. It was lyophilised at Wellcome Research Laboratories and assigned a culture number, BRD 519. The culture was obtained from Birmingham University.

Generation of a Defined Deletion of the Cloned *S. typhimurium* ssaV Gene

A plasmid (plasmid 7-2, Shea et al; PNAS, 1996; 93: 2593-2597) was generated by cloning a 7.5 kb PstI fragment isolated from *S. typhimurium* LT2 into the PstI site of pUC18. ssaV is positioned centrally on this fragment. A plasmid construct containing a defined deletion of the ssa V ORF was derived from plasmid 7-2 by using reverse orientation PCR. Primers annealing to the 5' (SEQ ID NO. 13) and 3' (SEQ ID NO. 14) regions of the ssaV open reading frame were designed to the *S. typhimurium* Spi2 sequence. An AvrII restriction site was incorporated into the 5' region of each primer and an XbaI site was incorporated into SEQ ID NO. 14. The XbaI site serves as a tag for the ssaV mutation so it can be detected easily by restriction analysis. The resulting PCR product was subjected to digestion with AvrII and the backbone plasmid molecules purified following agarose gel electrophoresis. Re-circularisation of the resulting fragments at the AvrII sticky-ends gave the required deletion construct designated pMDSV1. pMDSV1 contains a 5.5 kb PstI fragment with a defined 1894 bp deletion within the ssaV open reading frame, an AvrII and a XbaI restriction site are at the site of the deletion.

The suicide plasmid pCVD442 was used as a vector to introduce the ssaV deletion into the genome of *S. typhimurium* TML. The 5.5 kb PstI fragment containing the ssa V deletion was isolated from pMDSV1 and the ends made blunt by treatment with Klenow DNA polymerase. Plasmid pCVD442 was linearized by digestion with SmaI, treated with alkaline phosphatase and ligated to the blunt-ended fragments. The required construct was isolated and denoted pMDSV22.

pMDSV22 was introduced into *S. typhimurium* TML using conjugation. To this end the construct was transformed into the *E. coli* strain S17-1λ pir. The conjugation was performed according to standard procedures. Plasmid pMDSV22 was able to integrate into the TML genome following recombination between the homologous regions on the plasmid and the genome to give ampicillin resistant transconjugants. A transconjugate designated mdsv-WT2 was chosen for further manipulations. This transconjugant contains a copy of both the original wild-type ssaV and the deleted ssaV gene. It was grown in the absence of ampicillin to allow for a second recombination event to occur which would result in the loss of the pCVD442 DNA sequences and one copy of the ssa V gene, either the wild-type copy or the deleted copy. Isolates which had undergone this second recombination event were identified as ampicillin-sensitive derivatives which were able to grow in the presence of 5% sucrose (pCVD442 carries the sacB gene which when expressed results in a sucrose-sensitive phenotype). Strains that had retained only the deleted ssaV gene were identified by using PCR analysis. Primers having SEQ ID NO. 15 and SEQ ID NO. 16 gave a product of 2485 bp for the wild type ssa V and 591 bp for the deleted ssaV gene. Sequence analysis of the resulting PCR products confirmed the presence of the required deletion in 4 individual isolates, ZH20, ZH23, ZH25 and ZH26. These strains were stored in LB plus 15% glycerol at $-80°$ C. for long-term storage. Strain ZH26 was chosen for further manipulation.

Cloning the *S. typhimurium* aroC Gene from *S. Typhimurium* TML

Genomic DNA was isolated from *S. typhimurium* TML and cleaved with HindIII. HindIII fragments in the size range 5 to 6 kb were purified and ligated to HindIII-cleaved pBluescript. The ligation mixture was used to transform an *E. coli* aroC mutant, AB2849, and clones containing the *S. typhimurium* aroC gene were selected by virtue of their ability to complement this strain. Analysis of one clone, pDAC1, demonstrated that it contained a 5.2 kb HindIII fragment.

A defined 600 bp deletion was created within the cloned aroC gene by using PCR. The oligonucleotide primers were designed using the published DNA sequence of the *S. typhi* aroC gene (Acc. M27715). The DNA 5' to the aroC gene was amplified from pDAC1 using primers having SEQ ID NO. 19 and SEQ ID NO. 17. SEQ ID NO. 19 anneals to vector DNA, SEQ ID NO. 17 anneals to the 5' region of aroC. The DNA 3' to the aroC gene was amplified using primers having SEQ ID NO. 20 and SEQ ID NO. 18. SEQ ID NO. 20 anneals to vector DNA, SEQ ID NO. 18 anneals to the 3' region of aroC. The resulting PCR products had XbaI sites incorporated into the 5' ends to facilitate cloning. The fragments were cloned into the vector pUC18. The final plasmid construct pMIAC8 contains a defined deletion of aroC (Acc. M27715 position 544 to 1143) on a 4.8 kb HindIII fragment. The HindIII fragment is inserted at the HindIII site of pUC18. A single XbaI site is present at the site of the deletion.

Introduction of the aroC Mutation into the *S. Typhimurium* ssaV Mutant ZH26

The suicide plasmid pCVD442 was used as the vector to introduce the aroC deletion into the genome of *S. typhimurium* TML. The 4.8 kb HindIII fragment containing the aroC deletion was isolated from pMIAC8 and the ends made blunt by using the Stratagene DNA polishing kit (Part No. 200409). Plasmid pCVD442 was linearized by digestion with SmaI, treated with alkaline phosphatase and ligated to the blunt-ended fragments. The required construct was isolated and denoted pMCVC16. pMCVC16 was introduced into *S. typhimurium* ZH26 by using electroporation. Ampicillin-resistant transformants were selected and allowed to grow in the absence of ampicillin to allow for loss of the pCVD442 DNA sequences and one copy of the aroC gene, either the wild-type copy or the deleted copy. Strains that had undergone this second recombination event were identified as ampicillin-sensitive derivatives that were able to grow in the presence of 5% sucrose. Strains that had retained only the deleted aroC gene were initially identified as strains that were unable to grow on minimal media plates in the absence of a supplement of aromatic compounds. The aroC genotype was confirmed by using PCR analysis. Primers having SEQ ID NO. 21 and SEQ ID NO. 22 give a product of 994 bp for the wild type aroC and 400 bp for the deleted aroC gene. Sequence analysis of the resulting PCR products confirmed the presence of the required deletion in 4 individual isolates designated WT05, WT09, WT10 and WT12. Strain WT05 was chosen for manufacture of a CGMP master cell bank.

Example 3

The following construct was prepared to test the double mutant vaccines in an animal model. *S. typhimurium* SL1344, a strain that infects mice, was used, with single and double mutations present.

An ssaV::aph (non-polar) mutation from *S. typhimurium* 12023s was P22 transduced to SL1344 to give the single Spi2 mutant.

The aroC deletion/pCVD422 suicide vector pMCVC16 was electroporated into the *S. typhimurium* strain LB5010 and merodiploids were obtained. The aroC deletion merodiploid was then P22 transduced from the LB5010 merodiploid to SL1344. The SL1344 merodiploid was then resolved using sucrose selection to give the single aroC mutant.

The double mutant was generated by P22 transduction of the aroC deletion merodiploid from LB5010 into the SL1344 ssaV::aph. Plasmid sequences were resolved from the merodiploid leaving strain 3, the aroC deletion mutation in the SL1344 ssaV::aph background.

Pre-Clinical Pharmacodynamic Studies on Defined aroC/ssaV *Salmonella* Mutants

*Salmonella* mutants (strain SL1344) harbouring defined mutations in either aroC, ssaV or a combination of both mutations have been evaluated extensively in BALB/C mice to assess attenuation, persistence of the organisms and ability to immunise against challenge with the wild type strain.

Example 4

Animals Immunised by the Intravenous Route

Protection Studies

Groups of ten BALB/C mice were immunised i.v. with $10^5$ and $10^6$ organisms of SL1344 aroC, SL1344 ssaV, and SL1344 aroC: ssaV grown overnight in LB broth and resuspended in saline for administration. Mice were challenged 6 weeks later with $10^5$ wild type organisms given intravenously. Ten organisms of this wild type strain given intravenously are sufficient to kill mice.

All the mice given the single aroC or ssaV mutants were solidly protected after challenge with either dose and remained well throughout the experiment, exhibiting no sign of disease. For the double mutant 90% of the animals were solidly protected that received the immunisation with $10^6$ organisms. One of the animals died 8 days after the challenge. For the animals that were immunised with the lower dose, only 1 of the mice survived the challenge.

This experiment demonstrates that immunisation with *Salmonella* ssaV mutants, either alone, or in combination with an aroC mutation will immunise mice against challenge with the wild type *Salmonella* strain.

Persistence of Strains

Groups of mice were given $10^6$ organisms of the three *Salmonella* mutants described above. Four mice were sacrificed at different time points up to day 14 and enumeration of organisms in livers and spleens were performed. Counts of all three mutants were comparable up until day 10 when the counts were approximately $5\times10^5$ organisms in each organ. At day 14 a difference was demonstrated between the single mutants and the double mutants, there being a log less in the numbers of double mutant organisms in both liver and spleens.

The other important difference between the single mutant and the aroC/ssaV double mutant is that there were no liver abscesses present at any time during the experiment for the double mutants. However, the mice infected with the single mutants did have liver abscesses present at day 10 and 14. This is an important finding and strongly supports the use of this combination of mutations for evaluation the preparation of vaccines.

Immunogenicity

Mice immunised as above were bled and the antibody titres were determined against whole cell *Salmonella* using an ELISA. All three strains were demonstrated to be highly immunogenic, eliciting high titres of circulating IgG against *Salmonella*.

Example 5

Animals Immunised by the Oral Route

Persistence of Strains

Groups of mice immunised orally with $5\times10^9$ organisms of each of the three *Salmonella* mutants were sacrificed at periodic intervals and the numbers of organisms enumerated in livers and spleens. For the single aro mutant and the single ssaV mutant counts in livers and spleens were $10^3$ and $10^2$ respectively up until about day 21. Thereafter the numbers reduced. For the mice that received the aroC: ssaV double mutants, organisms were virtually undetectable in the livers and spleens after oral immunisation.

Oral Immunisation and Intravenous Challenge of A-J Mice Vaccinated with *Salmonella typhimurium* TML aroC/ssaV (WT05).

The purpose of this experiment was to ascertain the protective efficacy of $5\times10^9$ aroC/ssaV *S. typhimurium* TML mutants in an oral ity$^r$ murine vaccination and intravenous challenge model. This model more closely resembles the human response to *Salmonella* in that these animals are less susceptible than an ity$^s$ background.

$5\times10^9$ *S. typhimurium* TML aroC/ssaV in a volume of 0.2 ml PBS was inoculated orally by gavage tube into 10 6-8 week old A-J mice and left 8 weeks. Two mice were given PBS only at this time and served as control animals. After 8 weeks had elapsed the two immunised groups were challenged intravenously with $10^7$ wild type *S. typhimurium* TML. Mice were observed for 30 days post challenge.

All animals were solidly protected against wild type challenge (100% survival, 10/10 animals alive). Mice given PBS alone and then challenged with wild type *S. typhimurium* TML died on day 6 post challenge.

In an ity$^r$ background the double *S. typhimurium* TML aroC/ssaV seems to protect mice given an oral dose of $5\times10^9$. This may be important for the human situation as ity$^r$ mice are a better model of human salmonellosis, in terms of susceptibility to infection.

Studies were also carried out to evaluate the persistence of the double mutants in the livers and spleens of the mice. It was found that the double mutants persist at low levels to around day 21. By day 28, the mutant strain has been cleared.

Example 6

Human Clinical Trial 18 healthy volunteers were recruited to an open label, non-placebo controlled study. Following appropriate screening, each of 3 volunteers received a single oral dose of either $10^7$, $10^8$ or $10^9$ CFUs of *S. typhi* ZH9 or *S. typhimurium* WT05. The microorganisms prepared as above were resuspended to the appropriate dosing concentrations in a final volume of 100 ml of 2% (w/v) sodium bicarbonate solution to neutralize gastric acid. This liquid suspension was administered orally to the volunteers. The volunteers were then isolated for 72 hours, and then followed up post immunisation for safety and immunogenicity.

Volunteers were assessed for reactogenicity and other adverse events associated with vaccination by observation, physical examination and by the completion of diary cards. In addition, blood, stool and urine cultures were collected to assay for vaccinaemia, shedding and persistence of the vaccine strains. Additional safety data was obtained by measuring levels of C-reactive protein (CRP) and liver function enzymes (ALT) in blood, total white blood cell (WBC) counts and erythrocyte sedimentation rates (ESR) using standard procedures. These parameters were measured on blood taken daily until day 7 and then at weekly intervals until day 28.

Analysis of Mucosal and Systemic Immune Responses

Blood and saliva samples were collected prior to immunization and then on days, 7, 14, 21 and 28 after immunization, Saliva and serum were frozen at −70° C. until analysis by ELISA. Peripheral blood mononuclear cells were collected and assayed for the presence of antibody-secreting cells (ASCs) using the ELISPOT technique Both *S. typhi* ZH9 and *S. typhimurium* WT05 were well tolerated in all of the volunteers. No serious adverse events were noted in any of the volunteers at each of the 3 dose levels and blood and urine cultures remained negative in all vaccinees at all time-points examined. Thus, immunisation with both *S. typhi* ZH9 and *S. typhimurium* WT05 do not result in vaccinaemias. None of the volunteers given either of the strains developed diarrhoea or persistent high-grade fever, further indicating the safety of the vaccine strains. Persistent excretion nor vaccinaemia beyond day 7 was not observed in either of the 3 dose groups of *S. typhi* ZH9 or in the low dose (107) of *S. typhimurium* WT05.

Mucosal and Systemic Immune Responses Elicited by *S. Typhi* ZH9

Oral immunization with a single low dose ($1\times10^7$ CFUs) of *S. typhi* ZH9 resulted in the priming of *S. typhi*-specific IgA-secreting ASCs in 2 of 3 volunteers detected 7 days after immunization. Subsequent testing on days 14 and 21 showed that IgA ASCs were still detectable but at much lower levels and had disappeared by day 28. In almost all responder vaccinees, numbers of ASCs were highest on day 7. Surprisingly, ingestion of a higher dose ($10^8$ CFUs) of *S. typhi* ZH9 resulted in a low IgA ASC response in only one of three vaccinees. Ingestion of the highest dose ($1 \times 10^9$ CFUs) primed IgA ASCs in 2 of 3 volunteers.

*Salmonella*-Specific Serum Antibody Response

Oral immunization with a single low dose ($1 \times 10^7$ CFUs) of *S. typhi* ZH9 failed to elicit *S. typhi* LPS-specific serum IgG (despite generating IgA-ASCs in ⅔ vaccinees) when examined on days 7, 14, 21 and 28. Similarly only ⅓ produced very low levels of flagella-specific IgG. However, ingestion of $10^8$ CFUs resulted in the production of high levels of both LPS and flagella-specific IgG in all 3 volunteers. Increased levels of *S. typhi* LPS specific and flagella-specific were detected as early as 7 days after vaccination, rising on day 14 and remaining high on day 28. The highest dose of $10^9$ CFUs also stimulated LPS- and flagella-specific IgG in 2 of 3 vaccinees, detectable on days 7 and 14 respectively.

Conclusions

This study demonstrated the utility of the ssaV mutation, as a component of any new oral typhoid vaccine strain. An *S. typhi* strain harbouring aro mutations alone would have caused vaccinaemias at the doses given The ssaV mutation therefore provides an additional level of safety to the aro mutation alone by abolishing the vaccinaemias using this early formulation.

As well as proving to be well-tolerated, ZH9 was also demonstrated to be immunogenic at all three dose levels given. With regard to stimulating serum antibody, the intermediate ($10^8$ CFUs) and highest ($10^9$ CFUs) doses proved to be highly immunogenic, with ⅗ vaccines given $10^8$ CFUs and ⅔ given $10^9$ CFUs eliciting high titres of both *S. typhi* LPS and flagella specific-serum IgG. These responses are very encouraging since it is generally difficult to elicit serum antibody by oral vaccination.

As well as generating *S. typhi* specific serum antibody responses, ZH9 also primed IgA ASCs, indicative of immune stimulation at the intestinal mucosa. A total of 5/9 volunteers elicited an *S. typhi* LPS-specific IgA-secreting cell (ASC) response which did not appear to be dose-dependent.

WT05 was also well tolerated and no vaccinaemias were detected. Interestingly, no diarrhoeas or symptoms of gastroenteritis were detected in any of volunteers. The previous data obtained using the mutant TML strain with single aro or SPI 2 mutations in *S. typhimurium* given to mice suggested that a double aroC/ssaV mutant might cause some local intestinal effects e.g. diarrhoea, cramps in humans. The absence of these events further supports the utility of the combination of aro and SPI2 mutations.

Example 7

Heterologous Antigen Carriers

To demonstrate the utility of the ssaV:aroC double mutant strains to express and deliver foreign antigens, WT05 was transformed with a plasmid (pBRDO26) expressing the gene for the *E. coli* heat-labile enterotoxin B subunit (LT-B).

BALB/C mice (n=10/group) were immunised orally on days 0 and 28 with $10^9$CFUs (200 ml in PBS) WT05 expressing pBRD026, or with the WT05 vector strain (control). For comparison (and as a positive control) a group of mice (n=5) were immunised orally on days 0 and 28 with 10 μg purified LT (Sigma). Negative control mice (n=5) were immunise orally on days 0 and 28 with 200 μl PBS. Mice were bled from the tail vein on days 21, 28, and by cardiac puncture on day 42 and sera and intestinal lavage (day 42 only) collected and stored at −20° C.

All but one of the mice immunised with WT05/LT-B elicited LT-specific IgG (titres of 3,000-50,000) on day 28 after a single oral dose. None of the control mice immunisec orally with WT05 or PBS elicited LT-specific IgG. Oral immunisation with a single dose of purified LT elicited higher titres of LT-specific antibody (titres of 6,000->50,000). When the isotype of the LT-B-specific serum IgG was examined, it was found that the WT05 strain expressing pBRD026 elicited almost exclusively LT-specific IgG2a, indicating a bias towards a TH1-type immune response. In contrast, mice immunized with purified LT (Sigma) elicited almost exclusively LT-specific IgG1, indicating a TH2-type response. Therefore, expressing the LT-B within the aroC/ssaV strain facilitates profound immune modulation. The TH1-biased responses generated by the *Salmonella* aroC/ssaV strain will be important, when antigens from pathogenic organisms for which TH1-type responses are protective, are expressed.

We claim:

1. A method of preventing or treating a *Salmonella* infection comprising administering to a patient a composition comprising *Salmonella* microorganisms, each microorganism comprising an attenuating mutation which disrupts expression of an ssaV gene and an attenuating mutation which disrupts expression of an aro gene.

2. The method of claim 1, wherein said aro gene is aroC.
3. The method of claim 1, wherein said aro gene is aroA.
4. The method of claim 1, wherein said aro gene is aroD.
5. The method of claim 1, wherein said aro gene is aroE.
6. The method of claim 1, wherein said composition further comprises an adjuvant and/or a physiologically acceptable diluent.
7. The method of claim 1, wherein administering the composition prevents salmonellosis.
8. The method of claim 1, wherein administering the composition prevents typhoid fever.
9. The method of claim 1, wherein said *Salmonella* microorganisms are *S. typhi* or *S. typhimurium* microorganisms.
10. The method of claim 1, wherein said composition further comprises a buffering solution to neutralize stomach acid.
11. A method for treating an infection comprising administering to a patient a composition comprising *Salmonella* microorganisms, each microorganism comprising:
    (i) an attenuating mutation which disrupts expression of an ssaV gene;
    (ii) an attenuating mutation which disrupts expression of an aro gene; and
    (iii) a gene encoding a heterologous antigen.
12. The method of claim 11, wherein said aro gene is aroC.
13. The method of claim 11, wherein said aro gene is aroA.
14. The method of claim 11, wherein said aro gene is aroD.
15. The method of claim 11, wherein said aro gene is aroE.
16. The method of claim 11, wherein said composition further comprises an adjuvant and/or a physiologically acceptable diluent.
17. The method of claim 11, wherein said heterologous antigen is from a pathogenic organism selected from the group consisting of pathogenic *E. coli*, ETEC, *Shigella*, Hepatitis A, B or C Virus, Lime disease producing *Borrelia* sp., *Vibrio cholera*, *Helicobacter*, Herpes Simplex Virus and Human Papilloma Virus.
18. The method of claim 11, wherein said heterologous antigen is an *E. coli* heat-labile enterotoxin B subunit.
19. The method of claim 11, wherein administering the composition elicits a Th1-type immune response in the patient.

20. The method of claim 11, wherein the infection is a bacterial or viral infection.
21. The method of claim 11, wherein said *Salmonella* microorganisms are *S. typhi* or *S. typhimurium* microorganisms.
22. The method of claim 11, wherein said composition further comprises a buffering solution to neutralize stomach acid.
23. A method of inducing an immune response in a patient comprising administering to the patient a composition comprising *Salmonella* microorganisms, each microorganism comprising an attenuating mutation which disrupts expression of an ssaV gene and an attenuating mutation which disrupts expression of an aro gene.
24. The method of claim 23, wherein said each microorganism further comprises a gene encoding a heterologous antigen.
25. The method of claim 23, wherein said aro gene is aroC.
26. The method of claim 23, wherein said aro gene is aroA.
27. The method of claim 23, wherein said aro gene is aroD.
28. The method of claim 23, wherein said aro gene is aroE.
29. The method of claim 23, wherein said composition further comprises an adjuvant and/or a physiologically acceptable diluent.
30. The method of claim 24, wherein said heterologous antigen is from a pathogenic organism selected from the group consisting of pathogenic *E. coli*, ETEC, *Shigella*, Hepatitis A, B or C Virus, Lime disease producing *Borrelia* sp., *Vibrio cholera*, *Helicobacter*, Herpes Simplex Virus and Human Papilloma Virus.
31. The method of claim 24, wherein said heterologous antigen is an *E. coli* heat-labile enterotoxin B subunit.
32. The method of claim of claim 23 or 24, wherein said immune response is a Th1-type response.
33. The method of claim 23, wherein said *Salmonella* microorganisms are *S. typhi* or *S. typhimurium* microorganisms.
34. The method of claim 23, wherein said composition further comprises a buffering solution to neutralize stomach acid.
35. The method of claim 1, wherein said composition comprises about $10^7$ to about $10^{10}$ CFUs *Salmonella* CFUs.
36. The method of claim 23, wherein said composition comprises about $10^7$ to about $10^{10}$ CFUs *Salmonella* CFUs.
37. The method of claim 30, wherein said composition comprises about $10^7$ to about $10^{10}$ *Salmonella* CFUs.

* * * * *

SEQUENCE LISTING

<160> NUMBER OF SEQ ID NOS: 22

<210> SEQ ID NO 1
<211> LENGTH: 36
<212> TYPE: DNA
<213> ORGANISM: Artificial Sequence
<220> FEATURE:
<223> OTHER INFORMATION: Oligonucleotide

<400> SEQUENCE: 1
aatcagtcta gaaatactgg tgccggtcgt cacgcc                              36

<210> SEQ ID NO 2
<211> LENGTH: 36
<212> TYPE: DNA
<213> ORGANISM: Artificial Sequence
<220> FEATURE:

-continued

<223> OTHER INFORMATION: Oligonucleotide

<400> SEQUENCE: 2
aatcagtcta gaagtgggca acacattgtg gcgcat                        36

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide

<400> SEQUENCE: 3
cccagtcacg acgttgtaaa acg                                      23

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
agcggataac aatttcacac agg                                      23

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
cggcgaatca cacgggctgg c                                        21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
ggcgcagcag gtgatccatc a                                        21

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide

<400> SEQUENCE: 7
gccactaaca cgataacggt tgcgtgaaaa ccacg                         35

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide

<400> SEQUENCE: 8
tgtaaagtcc tctgcagaac cgagccagga gc                            32

```
<210> SEQ ID NO 9
<211> LENGTH: 61
<212> TYPE: DNA
<213> ORGANISM: Artificial Sequence
<220> FEATURE:
<223> OTHER INFORMATION: Oligonucleotide

<400> SEQUENCE: 9
caccgtccct aggaccatat cctgccgacc cgcgcataca ctgagccact gttgcgccct      60
g                                                                     61

<210> SEQ ID NO 10
<211> LENGTH: 63
<212> TYPE: DNA
<213> ORGANISM: Artificial Sequence
<220> FEATURE:
<223> OTHER INFORMATION: Oligonucleotide

<400> SEQUENCE: 10
ggcaggacct aggctagtct agacttatac aagtggtaga agtattgac cttagcgaag       60 agg                                                                   63

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
aatatgttct ggcggcaagg                                                 20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
atccccacga cttcagcaag                                                 20

<210> SEQ ID NO 13
<211> LENGTH: 61
<212> TYPE: DNA
<213> ORGANISM: Artificial Sequence
<220> FEATURE:
<223> OTHER INFORMATION: Oligonucleotide

<400> SEQUENCE: 13
caccgtccct aggaccatat cctgccgacc cgcgcataca ctgagccact gttgcgccct      60
g                                                                     61

<210> SEQ ID NO 14
<211> LENGTH: 63
<212> TYPE: DNA
<213> ORGANISM: Artificial Sequence
<220> FEATURE:
<223> OTHER INFORMATION: Oligonucleotide

<400> SEQUENCE: 14
ggcaggacct aggctagtct agacttatac aagtggtaga agtattgac cttagcgaag       60 agg                                                                   63
```

```
<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
aatatgttct ggcggcaagg                                              20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
atccccacga cttcagcaag                                              20

<210> SEQ ID NO 17
<211> LENGTH: 36
<212> TYPE: DNA
<213> ORGANISM: Artificial Sequence
<220> FEATURE:
<223> OTHER INFORMATION: Oligonucleotide

<400> SEQUENCE: 17
aatcagtcta gaaatactgg tgccggtcgt cacgcc                            36

<210> SEQ ID NO 18
<211> LENGTH: 36
<212> TYPE: DNA
<213> ORGANISM: Artificial Sequence
<220> FEATURE:
<223> OTHER INFORMATION: Oligonucleotide

<400> SEQUENCE: 18
aatcagtcta gaagtgggca acacattgtg gcgcat                            36

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide

<400> SEQUENCE: 19
cccagtcacg acgttgtaaa acg                                          23

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide

<400> SEQUENCE: 20
agcggataac aatttcacac agg                                          23

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide
```

-continued

```
<400> SEQUENCE: 21
cggcgaatca cacgggctgg c                                             21

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide

<400> SEQUENCE: 22
ggcgcagcag gtgatccatc a                                             21
```